(12) United States Patent
Kato

(10) Patent No.: US 8,731,645 B2
(45) Date of Patent: May 20, 2014

(54) IDENTIFICATION DEVICE

(75) Inventor: Hideo Kato, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 191 days.

(21) Appl. No.: 13/353,735

(22) Filed: Jan. 19, 2012

(65) Prior Publication Data

US 2012/0116239 A1    May 10, 2012

Related U.S. Application Data

(63) Continuation of application No. PCT/JP2009/064352, filed on Aug. 14, 2009.

(51) Int. Cl.
    *A61B 5/04*    (2006.01)
(52) U.S. Cl.
    USPC ........................................ 600/509
(58) Field of Classification Search
    USPC ................................ 600/508–509
    See application file for complete search history.

(56) References Cited

U.S. PATENT DOCUMENTS

| | | | |
|---|---|---|---|
| 2003/0189493 | A1 | 10/2003 | Klausner et al. |
| 2005/0239075 | A1* | 10/2005 | Yanagidaira et al. ............ 435/6 |
| 2008/0243013 | A1* | 10/2008 | Yanai et al. .................. 600/509 |

FOREIGN PATENT DOCUMENTS

| | | |
|---|---|---|
| JP | 2003-535757 | 12/2003 |
| JP | 2005-334106 | 12/2005 |
| JP | 2008-079939 | 4/2008 |
| JP | 2008-237379 | 10/2008 |
| JP | 2009-142575 | 7/2009 |
| WO | 01/94188 A1 | 12/2001 |

OTHER PUBLICATIONS

International Search Report for PCT/JP2009/064352, mailed Nov. 2, 2009.

* cited by examiner

*Primary Examiner* — Carl H Layno
*Assistant Examiner* — Paula J Stice
(74) *Attorney, Agent, or Firm* — Staas & Halsey LLP

(57) ABSTRACT

An identification device measures a potential difference signal between two contact electrodes contacted by a driver out of a plurality of electrodes installed in a handling unit or a potential difference signal between one contact electrode installed in the handling unit and a contact electrode different from the electrodes installed in the handling unit. The device identifies a contact electrode contacted by driver's hand out of the plurality of electrodes installed in the handling unit. The device determines whether the driver's hand in contact with the identified contact electrode is the right hand or the left hand on the basis of a rotational state of the handling unit and a position of the contact electrode in the handling unit. The device identifies the heart beat from the potential difference signal amplified by an amplification factor determined on the basis of a result of determination.

6 Claims, 14 Drawing Sheets

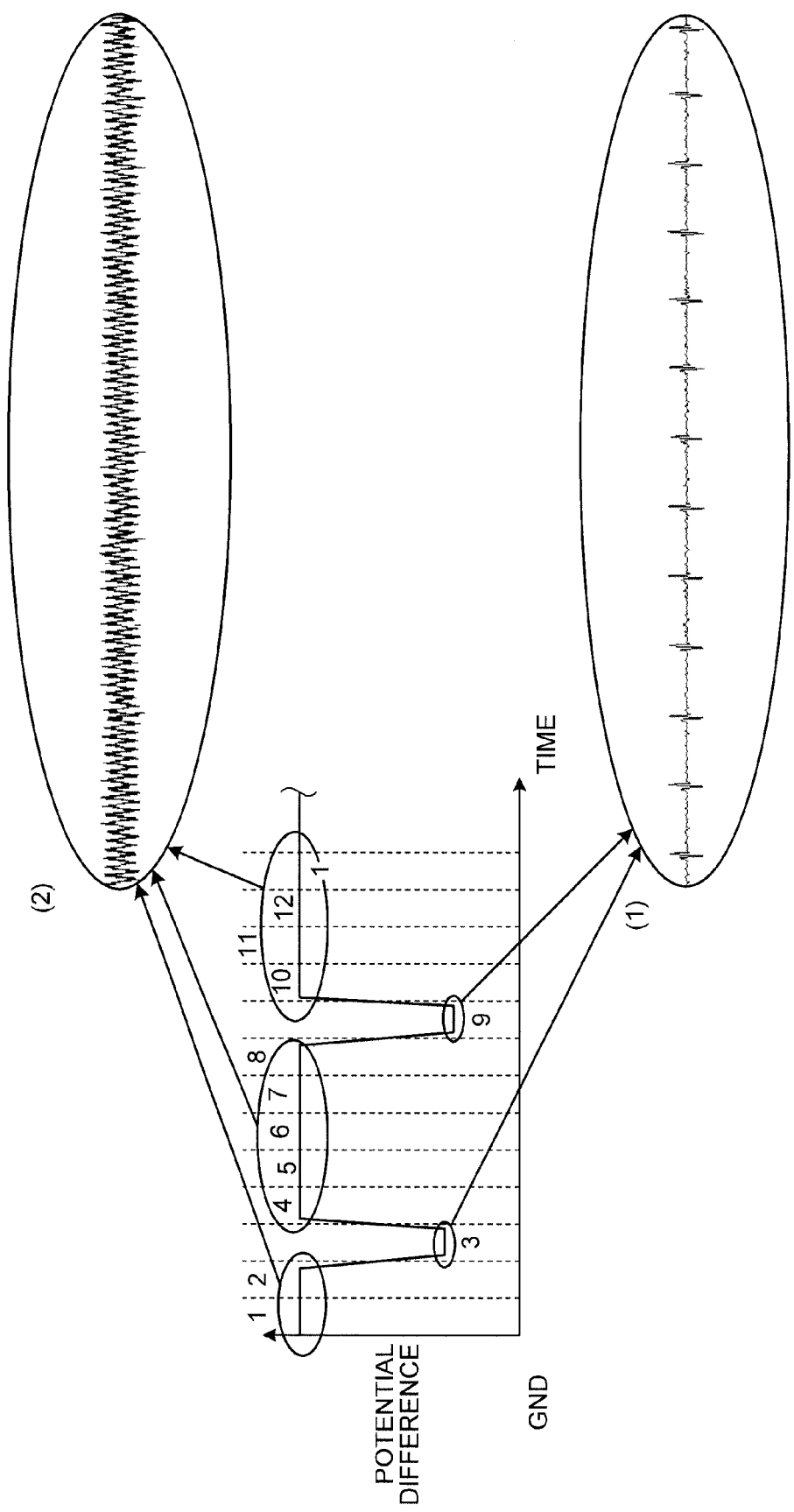

FIG.10

| TIME | IDENTIFICATION INFORMATION | DETERMINATION RESULT |
|---|---|---|
| ⋮ | ⋮ | ⋮ |
| 10:10:10 | 3 | RIGHT HAND |
|  | 9 | LEFT HAND |
|  |  |  |

IDENTIFICATION DEVICE

CROSS-REFERENCE TO RELATED APPLICATION

This application is a continuation of International Application No. PCT/JP2009/064352, filed on Aug. 14, 2009, the entire contents of which are incorporated herein by reference.

FIELD

The embodiments discussed herein are directed to an identification device.

BACKGROUND

Detecting a physiological state of a driver contributes to the deterrence of an accident due to the deterioration of the physiological state. Therefore, there is a detection method to detect a driver's physiological state using a state of driver's pulse or heartbeat. For example, a device that implements the detection method measures a potential difference signal between two electrodes in contact with a driver, and identifies a heart rate signal indicating driver's pulse or heartbeat from the measured potential difference signal. Then, the device detects the sleepiness or alertness, etc. as a physiological state of the driver using the identified heart rate signal.

A potential difference signal measured by the device that implements the detection method includes noise generated from other electronic devices installed in a vehicle and noise generated around the vehicle, and a heart rate signal included in the potential difference signal is weak. Therefore, the device that implements the detection method amplifies a potential difference signal by a predetermined amplification factor, and then identifies a heart rate signal.

To identify a weak heart rate signal, it is better to measure a potential difference signal using two positions resulting in a large potential difference as possible. Therefore, the device that implements the detection method measures a potential difference signal between electrodes located at two positions across the heart. The two positions across the heart are, for example, a combination of the right hand and the left hand, a combination of the right hand and the seat (the buttocks), a combination of the left hand and the seat, and the like.

For example, a plurality of electrodes to be contacted by a driver is installed in a steering part (a wheel) and a driver's seat, etc. of a vehicle. The electrode installed in the seat is contacted by driver's buttocks when a driver sits in the seat, and the electrode installed in the wheel is contacted by driver's hand when the driver holds the wheel, and then the device that implements the detection method measures a potential difference signal between the two electrodes.

Patent document 1: Japanese Laid-open Patent Publication No. 2008-237379

SUMMARY

According to an aspect of an embodiment of the invention, an identification device includes a measuring unit that measures a potential difference signal between two contact electrodes contacted by a driver out of a plurality of electrodes installed in a handling unit of equipment and/or a potential difference signal between one contact electrode out of the plurality of electrodes installed in the handling unit of the equipment and a contact electrode different from the electrodes installed in the handling unit. The identification device includes an electrode identifying unit that identifies a contact electrode contacted by the driver out of the plurality of electrodes installed in the handling unit. The identification device includes a determining unit that determines whether driver's hand in contact with the contact electrode identified by the electrode identifying unit is the right hand or the left hand on the basis of a rotational state of the handling unit and a position of the contact electrode in the handling unit. The identification device includes a beat identifying unit that identifies a heart beat from the potential difference signal amplified by an amplification factor determined on the basis of a result of determination by the determining unit.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

BRIEF DESCRIPTION OF DRAWINGS

FIG. 9 is a diagram for explaining about an example of information stored in a potential-difference storage unit in the second embodiment;

FIG. 10 is a diagram for explaining about an example of information stored in a determination-result storage unit in the second embodiment;

DESCRIPTION OF EMBODIMENTS

As described previously, the above-described detection detect a physiological state of a driver contributes to the deterrence of an accident due to the deterioration of the physiological state. However, the above-described detection method has a problem that a heart rate signal is apt to be buried in noise. The heart is located at a position slightly deviated from the center of body, and consequently the intensity of a heart rate signal included in a potential difference signal differs according to a combination of two positions across the heart. As a result, it is considered that an amplification factor suited to be used in identification of a heart rate signal from a potential difference signal also differs according to a combination of two positions across the heart. In the above-described detection method, whether the right hand or the left hand is in contact with the electrode installed in the wheel is not distinguished; therefore, it is not possible to apply an amplification factor suitable for a combination of the two positions of the electrodes, and the heart rate signal is apt to be buried in noise.

Preferred embodiments of the present invention will be explained with reference to accompanying drawings.

Incidentally, this invention is not limited to the embodiments. The embodiments can be arbitrarily combined within a scope which does not contradict the processing contents.

[a] First Embodiment

Figure 1:
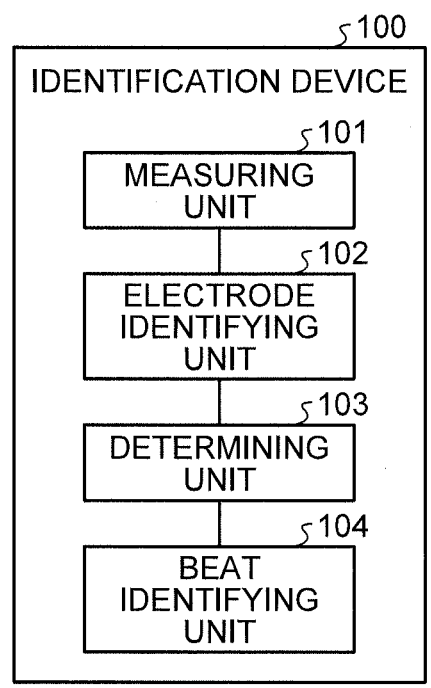
FIG. 1 is a block diagram for explaining about an example of a configuration of an identification device according to a first embodiment.

First of all, an example of a configuration of an identification device 100 according to a first embodiment is explained with reference to FIG. 1. FIG. 1 is a block diagram for explaining about an example of a configuration of an identification device according to the first embodiment. In the example illustrated in FIG. 1, the identification device 100 has a measuring unit 101, an electrode identifying unit 102, a determining unit 103, and a beat identifying unit 104.

The measuring unit 101 measures a potential difference signal between two contact electrodes contacted by a driver out of a plurality of electrodes installed in a steering part of equipment. Furthermore, the measuring unit 101 measures a potential difference signal between one contact electrode out of the plurality of electrodes installed in the steering part of the equipment and a contact electrode different from the electrodes installed in the steering part.

The electrode identifying unit 102 identifies a contact electrode contacted by driver's hand out of the plurality of electrodes installed in the steering part. Then, the determining unit 103 determines whether the driver's hand in contact with the contact electrode identified by the electrode identifying unit 102 is the right hand or the left hand on the basis of a rotational state of the steering part and a position of the contact electrode in the steering part.

The beat identifying unit 104 identifies the heart beat from a potential difference signal amplified by an amplification factor determined on the basis of a result of determination by the determining unit 103.

Namely, when a user holds the steering part in which electrodes are installed, the identification device 100 according to the first embodiment determines whether the right hand or the left hand is in contact with an electrode from a position of the electrode in contact with the hand and a rotation angle of the steering part, and identifies the heart beat using an amplification factor suitable for the determined hand.

As described above, according to the first embodiment, it is possible to distinguish whether the right hand or the left hand is in contact with an electrode installed in the steering part. The heart is located at a position slightly deviated from the center of body, and consequently the intensity of a heart rate signal included in a potential difference signal differs according to a combination of two positions across the heart. As a result, it is considered that an amplification factor suited to be used in identification of a heart rate signal from a potential difference signal also differs according to a combination of two positions across the heart. According to the first embodiment, it is possible to distinguish whether the right hand or the left hand is in contact with an electrode, and consequently the heart beat can be identified by using an amplification factor suitable for a combination of two positions of electrodes between which a potential difference signal is measured, and a weak heart rate signal which is apt to be buried in noise can be identified with a high degree of accuracy. Furthermore, no matter whether driver's hand in contact with an electrode is the right hand or the left hand, a heart rate signal can be detected with accuracy; therefore, it is possible to increase duration of detection of a heart rate signal.

Incidentally, in the embodiment, there is described the steering part installed in a vehicle as an example. However, an object equipped with the steering part does not have to be limited to a vehicle as long as the steering part is a part continuously and electrically contacted by both hands or one hand of a person who is an object of detection of an heart beat, and the part does not have to be limited to a steering part.

[b] Second Embodiment

Configuration of Identification Device According to Second Embodiment

Figure 2:
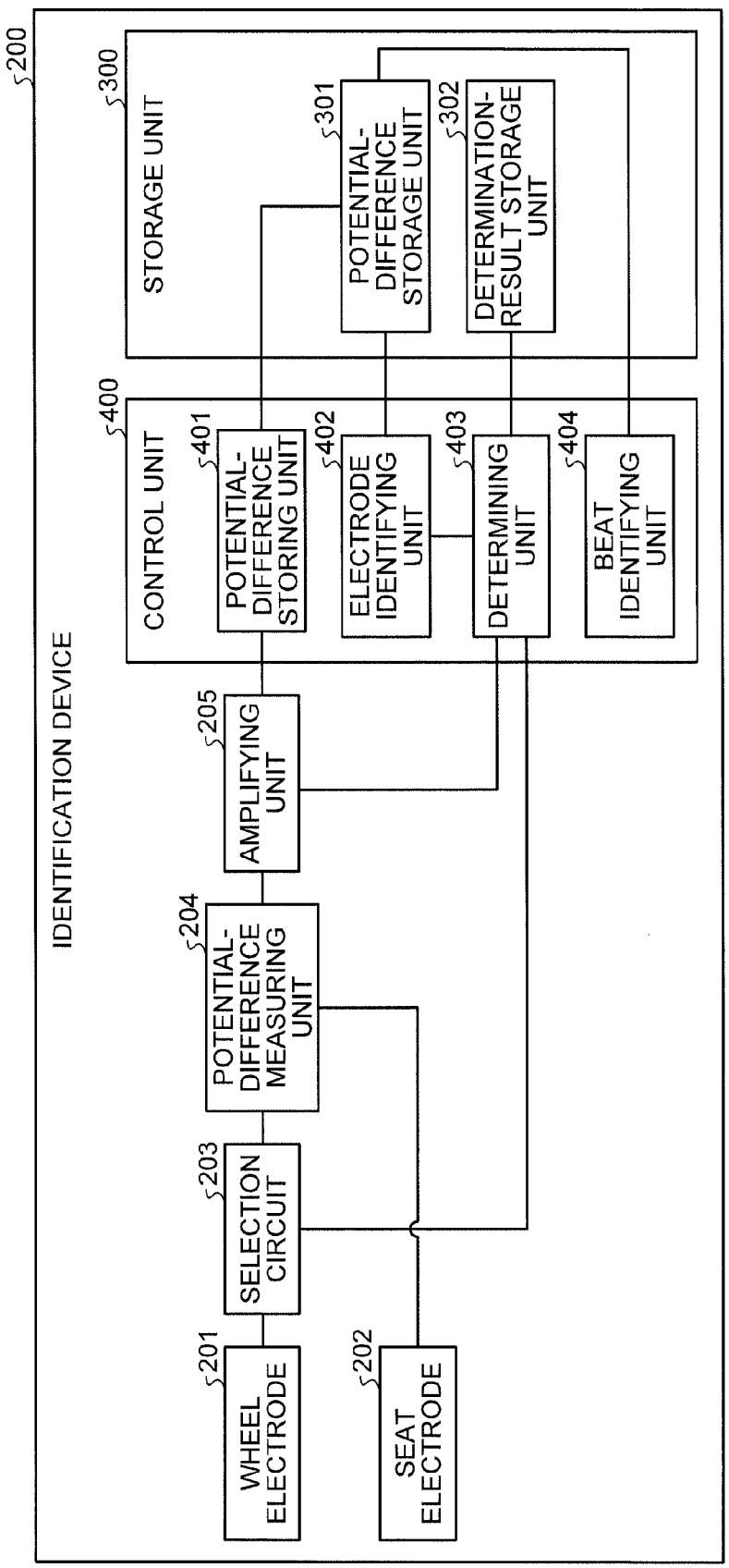
FIG. 2 is a block diagram for explaining about an example of a configuration of an identification device according to a second embodiment.

Subsequently, an identification device 200 according to a second embodiment is explained. First, an example of a configuration of the identification device 200 according to the second embodiment is explained with reference to FIG. 2. FIG. 2 is a block diagram for explaining about an example of a configuration of an identification device according to the second embodiment. In the example illustrated in FIG. 2, the identification device 200 according to the second embodiment has a wheel electrode 201, a seat electrode 202, a selection circuit 203, a potential-difference measuring unit 204, an amplifying unit 205, a storage unit 300, and a control unit 400.

Figure 3:
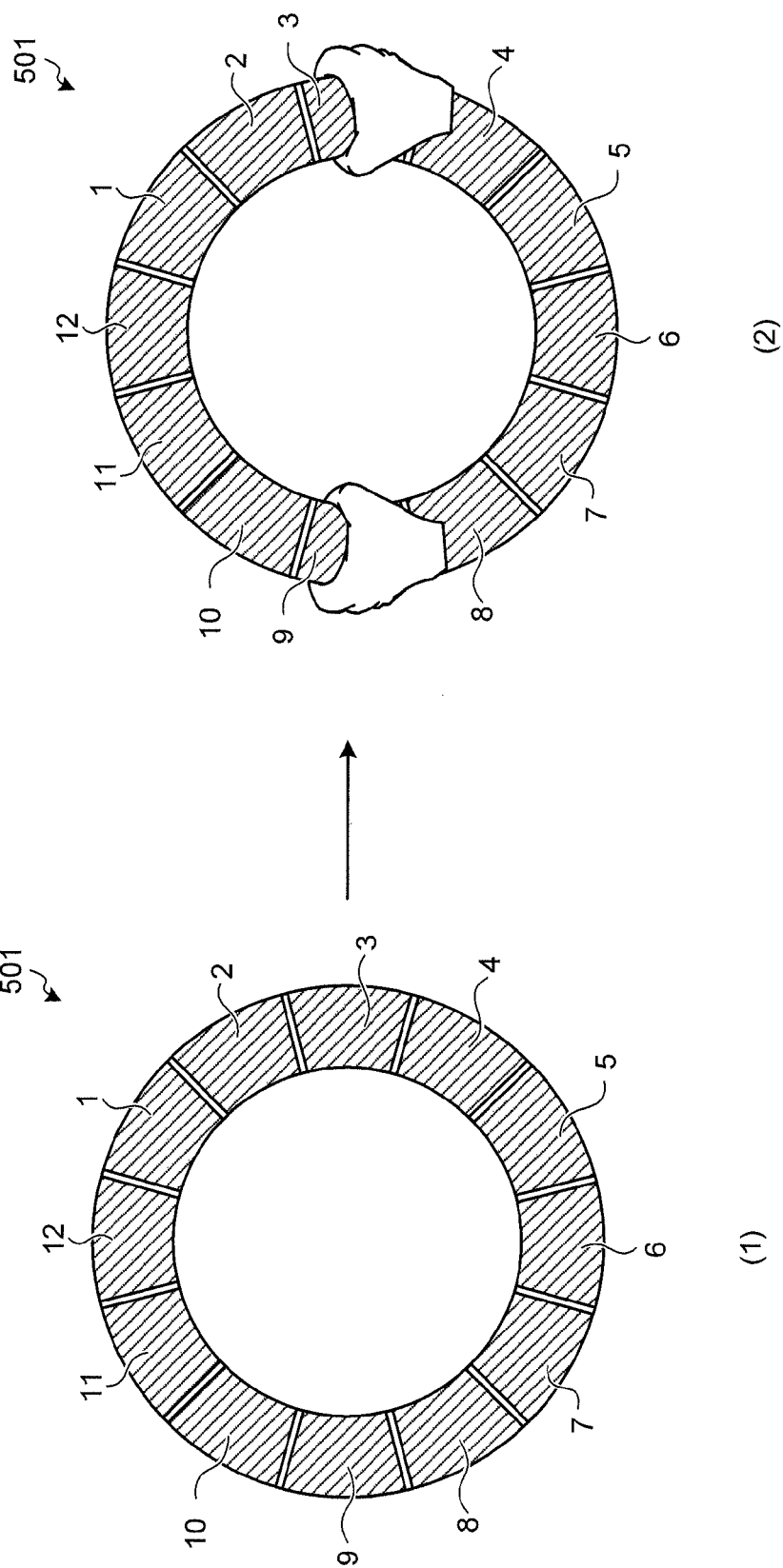
FIG. 3 is a diagram for explaining about an example of a wheel electrode in the second embodiment.

The wheel electrode 201 is connected to the selection circuit 203. Furthermore, a plurality of the wheel electrodes 201 is installed in a steering wheel 501 of a vehicle. Incidentally, the steering wheel 501 is also referred to as a steering part and a steering wheel. Here, an example of the structure of the wheel electrode 201 is explained with reference to FIG. 3. FIG. 3 is a diagram for explaining about an example of a wheel electrode in the second embodiment. In FIG. 3, as an example, there is illustrated a case where twelve uniformly-sized wheel electrodes 201 are installed along a circumferential direction of the steering wheel 501. Numbers "1" to "12" in FIG. 3 denote the wheel electrodes 201. Incidentally, in the description below, there is described taking for example a case where "twelve" wheel electrodes 201 are installed in the steering wheel 501 unless otherwise noted. Furthermore, in the description below, the "twelve" wheel electrodes 201 are denoted by the wheel electrode "1", the wheel electrode "2", . . . , the wheel electrode "12", respectively.

To return to FIG. 2, when the steering wheel 501 is held by a driver, the wheel electrode 201 is contacted by the driver. In an example illustrated in (2) of FIG. 3, the wheel electrode "3" is contacted by driver's right hand, and the wheel electrode "9" is contacted by driver's left hand.

The wheel electrode 201 detects its own electric potential with an electric potential of the vehicle as a reference potential. Specifically, the plurality of wheel electrodes 201 detect their own electric potential. More specifically, a wheel electrode 201 contacted by driver's hand out of the wheel electrodes 201 detects an electric potential of the driver's hand with an electric potential of the vehicle as a reference potential.

Furthermore, the wheel electrode 201 sends the detected electric potential to the selection circuit 203. Specifically, the wheel electrode 201 periodically detects an electric potential, and each time the wheel electrode 201 detects an electric potential, the wheel electrode 201 sends the detected electric potential.

Figure 4:
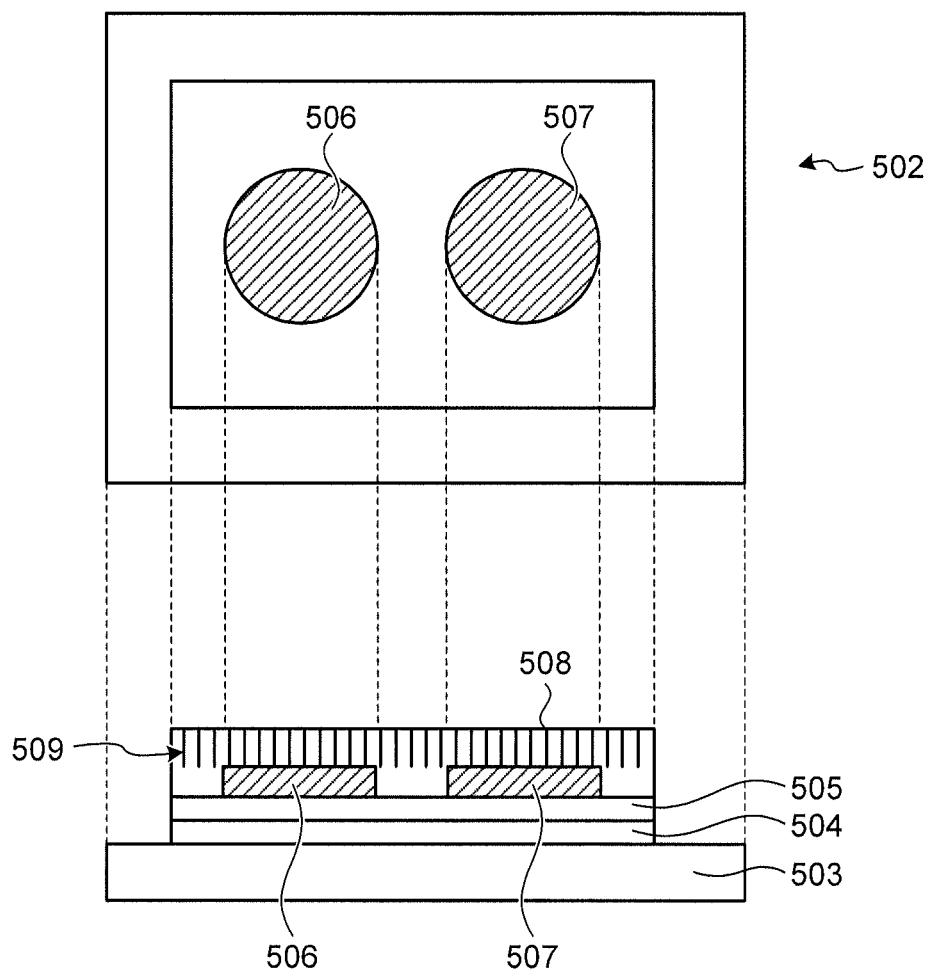
FIG. 4 is a diagram for explaining about an example of a seat electrode installed in a seat in the second embodiment.

The seat electrode 202 is connected to the potential-difference measuring unit 204. An example of the structure of the seat electrode 202 is explained with reference to FIG. 4. FIG. 4 is a diagram for explaining about an example of a seat electrode installed in a seat in the second embodiment. The seat electrode 202 is an electrode different from the electrodes installed in the steering wheel 501, and is installed in a seat 502 of the vehicle. In the example illustrated in FIG. 4, the seat electrode 202 has the structure that a lower electrode 504, an insulating layer 505, upper electrodes 506 and 507, and a protective member 508 are sequentially stacked on a seat member 503 which is a member of the seat 502.

Here, a conductive part 509 is installed in the protective member 508. The conductive part 509 is connected to the upper electrodes 506 and 507. Incidentally, the conductive part 509 is installed, for example, on an inner wall of a hole part having an opening formed on the protective member 508. The upper electrodes 506 and 507 detect an electric state from the right and left sides of the driver's buttocks, respectively.

The lower electrode 504 is grounded, and is opposed to the upper electrodes 506 and 507 via the insulating layer 505. As a result, a combination of the upper electrode 506 or 507 and the lower electrode 504 serves as an electrode installed in the seat 502.

Incidentally, in the description below, there is described taking for example a case of not distinguishing between the upper electrodes 506 and 507; however, the present embodiment is not limited to this case. For example, the upper electrodes 506 and 507 can be electrically independent and independently detect an electric state from the right and left sides of the driver's buttocks, respectively. Furthermore, in the case where the upper electrodes 506 and 507 are electrically independent, an individual lower electrode can be installed with respect to each upper electrode.

The seat electrode 202 is contacted by the driver when the driver sits in the seat 502. In the example illustrated in FIG. 4, the seat electrode 202 is contacted by the driver in such a way that the driver sits in the seat 502, and consequently the upper electrodes 506 and 507 are contacted by the driver's buttocks via the conductive part 509. Incidentally, in the second embodiment, there is described taking for example a case where the seat electrode 202 is being contacted by the driver unless otherwise noted. Namely, there is described taking for example a case where the driver is sitting in the seat 502.

The seat electrode 202 detects its own electric potential with an electric potential of the vehicle as a reference potential. For example, the seat electrode 202 detects an electric potential of the driver's buttocks when the seat electrode 202 is contacted by the driver's buttocks and bases an electric potential of the vehicle as a reference potential. Then, the seat electrode 202 sends the detected electric potential to the potential-difference measuring unit 204. Specifically, the seat electrode 202 periodically detects an electric potential, and each time the seat electrode 202 detects an electric potential, the seat electrode 202 sends the detected electric potential.

Incidentally, the seat electrode 202 can be an electrode installed in a position other than the seat 502 as long as the position can be in continuous and electrical contact with a part of the body located on the different side of the hand across the heart of a person who is an object of detection of a heart beat.

Figure 5:
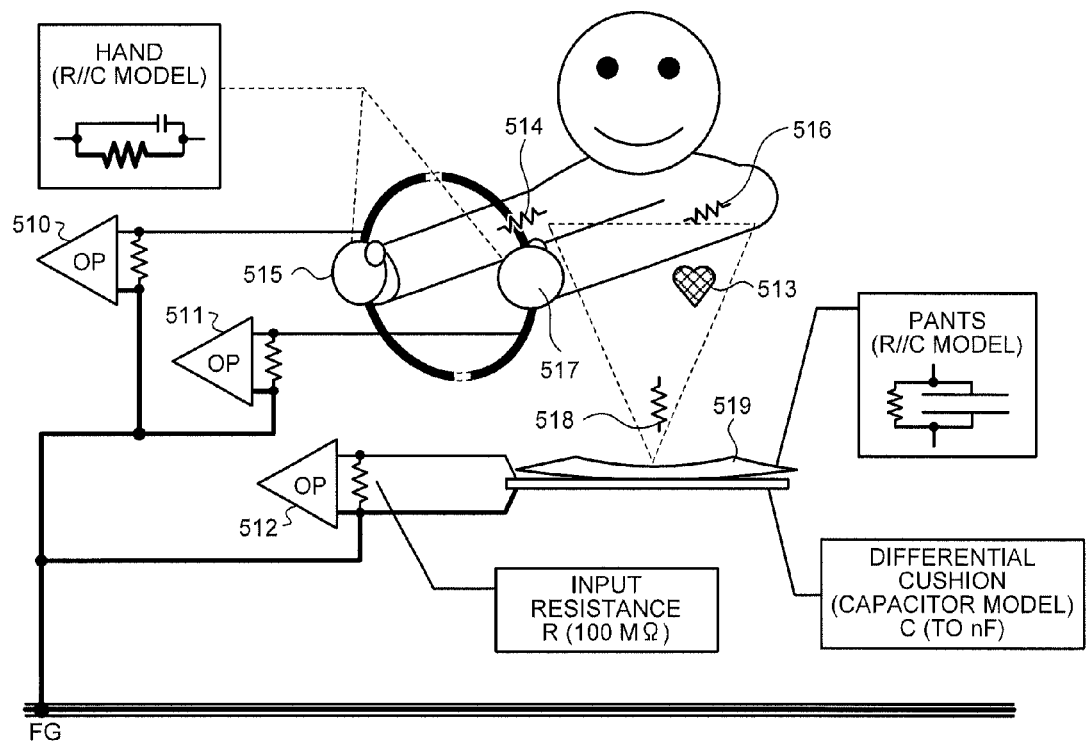
FIG. 5 is a diagram for explaining how the wheel electrode and the seat electrode in the second embodiment detect an electric state.

How the wheel electrode 201 and the seat electrode 202 detect an electric potential is explained with reference to FIG. 5. FIG. 5 is a diagram for explaining how the wheel electrode and the seat electrode in the second embodiment detect an electric potential. In FIG. 5, for the convenience of explanation, there is described taking for example a case where "two" wheel electrodes 201 are installed in the steering wheel 501 and the "two" wheel electrodes 201 are contacted by driver's right and left hands, respectively.

Here, a part from heart 513 to the arm of a driver is electrically considered as a resistance component. Driver's hand is electrically considered as a resistor capacitor (RC) parallel circuit. A part from the heart 513 to the buttocks of the driver is electrically considered as a resistance component. Furthermore, clothes, such as pants or a skirt, is electrically considered as an RC parallel circuit. As a result, an equivalent circuit including the driver himself is as illustrated in FIG. 5. Incidentally, in FIG. 5, a resistance component from the heart 513 to the right arm of the driver is denoted by a resistance 514; the right hand is denoted by an RC parallel circuit 515; a resistance component from the heart 513 to the left arm of the driver is denoted by a resistance 516; the left hand is denoted by an RC parallel circuit 517. Furthermore, a resistance component from the heart 513 to the buttocks is denoted by a resistance 518, and the clothes is denoted by an RC parallel circuit 519. Moreover, an operational amplifier is denoted by "OP".

As illustrated in FIG. 5, an operational amplifier 510 has two inputs. A cardiac action potential of the heart 513 is input to one of the inputs of the operational amplifier 510 via the resistance 514 and the RC parallel circuit 515, and an electric potential of a vehicle body frame, which is a reference potential, is input to the other input. Then, the operational amplifier 510 amplifies the cardiac action potential with the electric potential of the vehicle body frame as a reference potential, and outputs the amplified cardiac action potential. Furthermore, in the same manner as the operational amplifier 510, a cardiac action potential of the heart 513 is input to an operational amplifier 511 via the resistance 516 and the RC parallel circuit 517, and the operational amplifier 511 amplifies the cardiac action potential and then outputs the cardiac action potential. Moreover, in the same manner as the operational amplifier 510, a cardiac action potential of the heart 513 is input to an operational amplifier 512 via the resistance 518 and the RC parallel circuit 519, and the operational amplifier 512 amplifies the cardiac action potential and then outputs the cardiac action potential.

Namely, in the example illustrated in FIG. 5, the operational amplifier 510 detects a cardiac action potential from the driver's right hand, and amplifies the detected cardiac action potential and then sends the cardiac action potential to the selection circuit 203. The operational amplifier 511 detects a cardiac action potential from the driver's left hand, and amplifies the cardiac action potential and then sends the cardiac action potential to the selection circuit 203. The operational amplifier 512 detects a cardiac action potential from the driver's buttocks, and amplifies the cardiac action potential and then sends the cardiac action potential to the potential-difference measuring unit 204.

Incidentally, the reason why the operational amplifiers 510 to 512 send a cardiac action potential after amplifying the cardiac action potential is because based on an electric potential of the vehicle body frame as a reference potential, a cardiac action potential is weak. Furthermore, the operational amplifiers 510 to 512 amplify a cardiac action potential by a fixed amplification factor.

To return to FIG. 2, the selection circuit 203 is connected to the wheel electrode 201, the potential-difference measuring unit 204, and the control unit 400. The selection circuit 203 receives an electric potential from each of the plurality of wheel electrodes 201 installed in the steering wheel 501, and sends the received electric potential to the potential-difference measuring unit 204.

Specifically, the selection circuit 203 sends the electric potential received from any of the wheel electrodes 201 to the potential-difference measuring unit 204 instead of sending all the electric potentials received from the plurality of wheel electrodes 201 at the same time. Furthermore, the selection circuit 203 switches the wheel electrode 201 as a transmission source of electric potential to be sent to the potential-difference measuring unit 204 at every predetermined timing.

Figure 6:
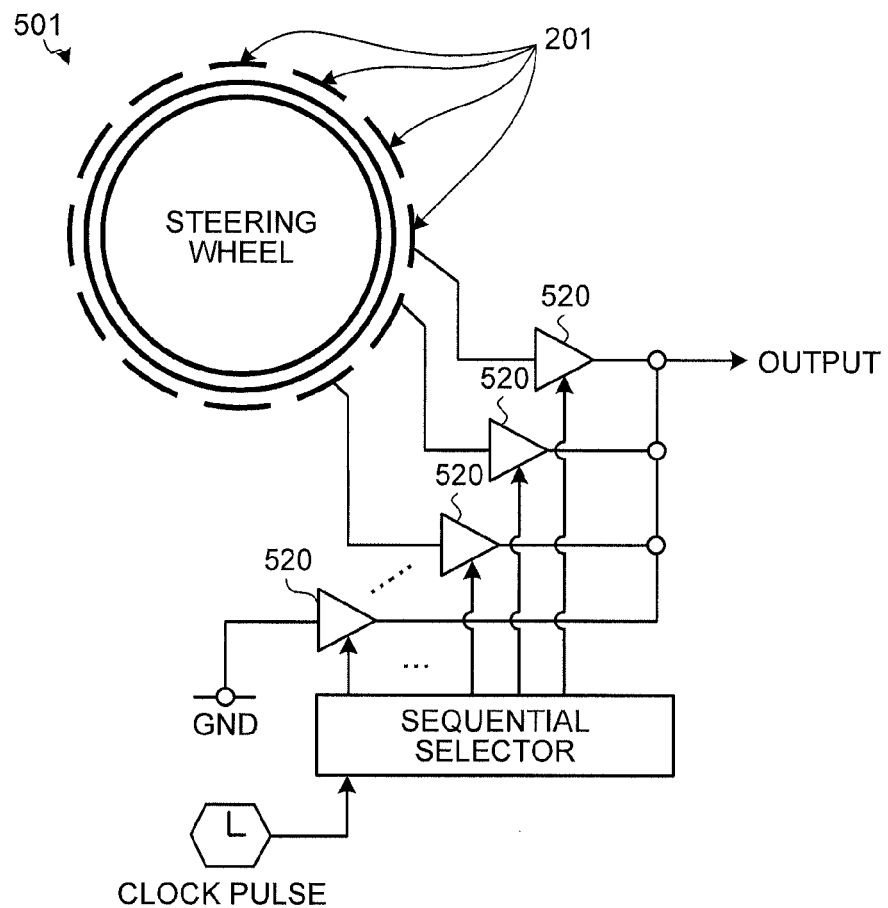
FIG. 6 is a diagram for explaining about an example of a selection circuit in the second embodiment.

Here, an example of the selection circuit 203 is further explained with reference to FIG. 6. FIG. 6 is a diagram for explaining about an example of a selection circuit in the second embodiment. In FIG. 6, for the convenience of explanation, the steering wheel 501 and the wheel electrodes 201 are also illustrated. In the example illustrated in FIG. 6, the selection circuit 203 has analog switches 520 respectively corresponding to the wheel electrodes 201 installed in the steering wheel 501. The selection circuit 203 sets one of the analog switches 520 to "ON". As a result, the selection circuit 203 sends an electric potential received from the wheel electrode 201 corresponding to the analog switch 520 set to "ON" to the potential-difference measuring unit 204. Furthermore, when setting one of the analog switches 520 to "ON", the selection circuit 203 sets the other analog switches 520 to "OFF". As a result, the selection circuit 203 does not send electric potentials received from the wheel electrodes 201 corresponding to the analog switches 520 set to "OFF" to the potential-difference measuring unit 204. Incidentally, as "GND" in FIG. 6 suggests, there is illustrated an example where the selection circuit 203 has analog switches connected to the ground.

Furthermore, for example, the selection circuit 203 changes the analog switch 520 to be set to "ON" with every predetermined time. More specifically, the selection circuit 203 changes the wheel electrode 201 as a detection source of an electric signal to be sent to the potential-difference measuring unit 204 sequentially in the order from the wheel electrode "1" to the wheel electrode "12". After changing to the wheel electrode "12", the selection circuit 203 next changes to the wheel electrode "1", and repeats the process to change the wheel electrode 201 as a detection source.

To return to FIG. 2, the potential-difference measuring unit 204 is connected to the selection circuit 203, the seat electrode 202, and the amplifying unit 205. The potential-difference measuring unit 204 measures a difference in potential between a contact electrode contacted by the driver out of the plurality of wheel electrodes 201 installed in the steering wheel 501 of the vehicle and the seat electrode 202 contacted by the driver.

Specifically, first, the potential-difference measuring unit 204 receives an electric potential detected by the wheel electrode 201 from the selection circuit 203, and also receives an electric potential detected by the seat electrode 202 from the seat electrode 202. Then, the potential-difference measuring unit 204 measures a potential difference between the electric potential received from the selection circuit 203 and the electric potential received from the seat electrode 202. As a result, if any of the wheel electrodes 201 is being held by the driver, the potential-difference measuring unit 204 receives an electric potential of the contact electrode, and measures a potential difference between the contact electrode and the seat electrode 202.

Figure 7:
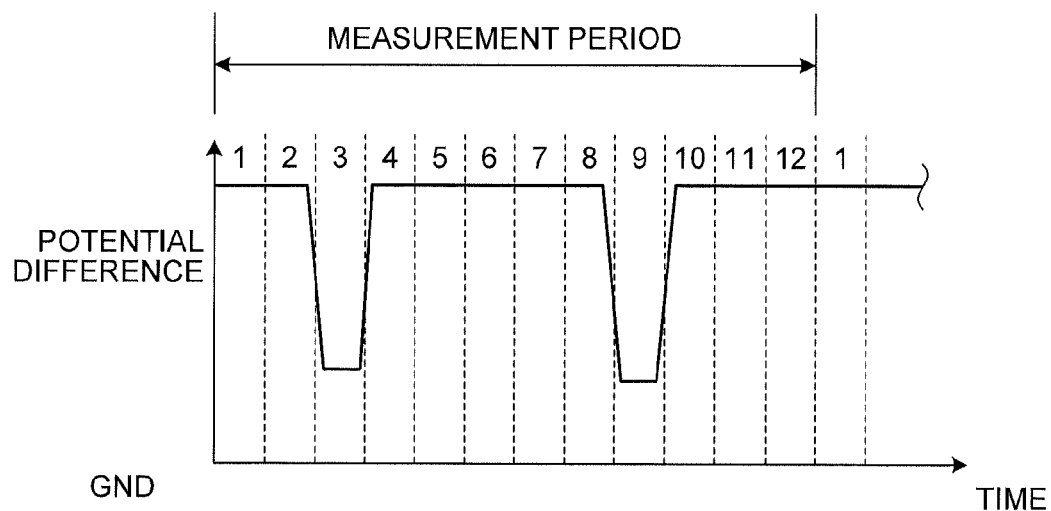
FIG. 7 is a diagram for explaining about an example of a potential difference signal sent to an amplifying unit by a potential-difference measuring unit in the second embodiment.

Furthermore, the potential-difference measuring unit 204 sends the measured potential difference to the amplifying unit 205. The potential difference sent by the potential-difference measuring unit 204 is further explained with reference to FIG. 7. FIG. 7 is a diagram for explaining about an example of a potential difference signal sent to an amplifying unit by a potential-difference measuring unit in the second embodiment. In FIG. 7, the vertical axis indicates a potential difference, and the horizontal axis indicates the time axis. In the description below, without limiting a potential difference to a value of potential difference at a certain moment, each of values of potential difference continuously measured from a certain time-position is referred to as a potential difference signal.

Here, "measurement period" in FIG. 7 denotes a period of time for one round of the output of potential difference signals measured using electric potentials detected by the plurality of wheel electrodes 201. Namely, the "measurement period" in FIG. 7 denotes a time from when the output of a potential difference signal on the wheel electrode "1" is started till when the output of a potential difference signal on the wheel electrode "12" is completed. In the example illustrated in FIG. 7, "1" on the time axis in FIG. 7 denotes a potential difference signal on the wheel electrode "1", and "2" on the time axis in FIG. 7 denotes a potential difference signal on the wheel electrode "2".

Incidentally, the plurality of wheel electrodes 201 is installed in the steering wheel 501; some of the wheel electrodes 201 are contacted by the driver's hands and others are not. Here, a value of potential difference on a contact electrode contacted by driver's hand is different from a value of potential difference on a non-contact electrode not contacted by driver's hand.

Specifically, the driver is in contact with the vehicle. Therefore, when the wheel electrode 201 is contacted by the driver, the wheel electrode 201 detects an electric potential close to a reference potential which is an electric potential of the vehicle. In other words, a contact electrode detects a value closer to the reference potential as compared with an electric potential detected by a non-contact electrode. Furthermore, the seat electrode 202 is contacted by driver's buttocks. Therefore, the seat electrode 202 detects a value closer to the reference potential than an electric potential detected by a non-contact electrode.

As a result, a value of potential difference between an "electric potential detected by the seat electrode 202" and an "electric potential detected by a contact electrode" is smaller than a potential difference between an "electric potential detected by the seat electrode 202" and an "electric potential detected by a non-contact electrode". For example, when the wheel electrodes "3" and "9" are contacted by driver's hands, as illustrated in FIG. 7, a potential difference on the wheel electrode "3" and a potential difference on the wheel electrode "9" are smaller than potential differences on the other wheel electrodes 201.

To return to FIG. 2, the amplifying unit 205 is connected to the potential-difference measuring unit 204 and the control unit 400. The amplifying unit 205 receives a potential difference signal measured by the potential-difference measuring unit 204. Then, the amplifying unit 205 performs various filtering on the received potential difference signal, thereby reducing noise included in the received potential difference signal. Namely, the amplifying unit 205 reduces components other than a component related to cardiac action potential out of components included in the received potential difference signal.

For example, the amplifying unit 205 performs filtering using a notch filter, a band-pass filter, and a correlation filter sequentially. Incidentally, the notch filter is a filter that attenuates a signal of a particular frequency. The band-pass filter is a filter that allows passage of a particular frequency. The correlation filter is a filter that performs back-diffusion processing (correlation processing) on a signal.

A difference between before and after a filtering process performed by the amplifying unit 205 is explained with reference to FIGS. 8A to 8D. FIGS. 8A to 8D are diagrams for explaining about a difference between before and after the filtering process. Incidentally, in FIGS. 8A to 8D, the vertical axis indicates a potential difference, and the horizontal axis indicates the time axis. In examples illustrated in FIGS. 8A to 8D, data measured when a resistance value of a part from the seat to driver's right hand is "200 kΩ" is illustrated as an example.

Figure 8A:
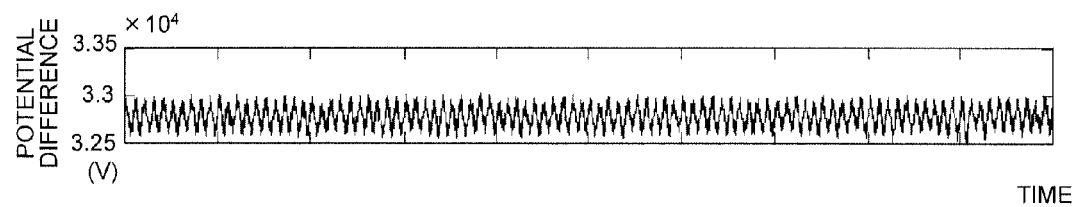
FIG. 8A is a diagram for explaining about a difference between before and after a filtering process.

First, FIG. 8A illustrates a potential difference signal when the amplifying unit 205 has received it from the potential-difference measuring unit 204. Namely, FIG. 8A illustrates an example of a potential difference signal before a filtering process is performed on the potential difference signal by the amplifying unit 205. Incidentally, for the convenience of explanation, the potential difference signal illustrated in FIG. 8A shall be a potential difference signal on a contact electrode. For example, the potential difference signal illustrated in FIG. 8A is a potential difference signal that the potential difference signal on the wheel electrode "3" or "9" on the time axis in FIG. 7 is enlarged.

Figure 8B:
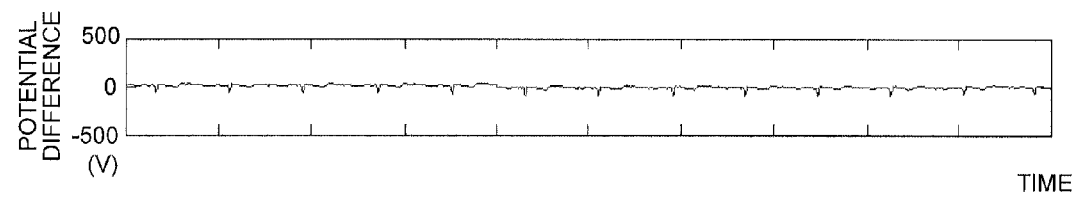
FIG. 8B is a diagram for explaining about a difference between before and after a filtering process.
Figure 8C:
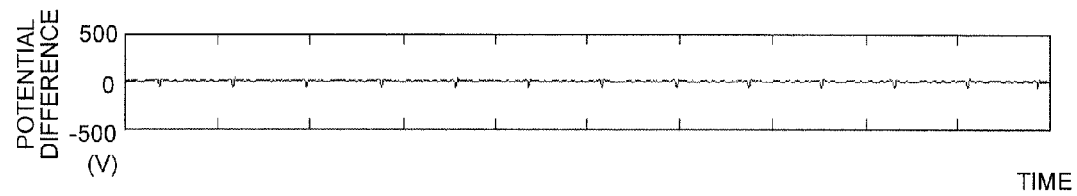
FIG. 8C is a diagram for explaining about a difference between before and after a filtering process.
Figure 8D:
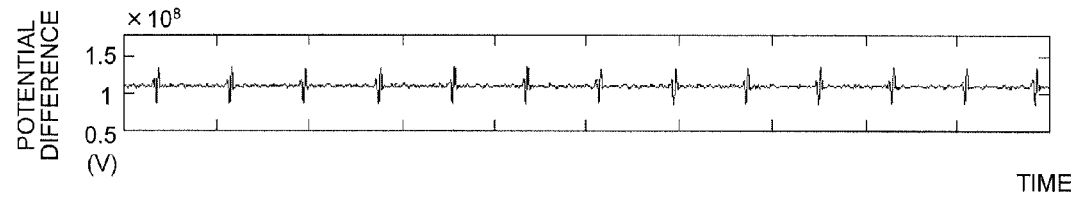
FIG. 8D is a diagram for explaining about a difference between before and after a filtering process.

Then, FIG. 8B illustrates a potential difference signal obtained by performing a filtering process using the notch filter on the potential difference signal illustrated in FIG. 8A. Then, FIG. 8C illustrates a potential difference signal obtained by performing a filtering process using the band-pass filter on the potential difference signal illustrated in FIG. 8B. Then, FIG. 8D illustrates a potential difference signal obtained by performing a filtering process using the correlation filter on the potential difference signal illustrated in FIG. 8C.

As illustrated in FIG. 8A, the potential difference signal when the amplifying unit 205 has received it from the potential-difference measuring unit 204 includes a lot of noise, and is not in a state where a component related to cardiac action potential can be easily identified. However, as illustrated in FIGS. 8B to 8D, after the various filtering processes are performed on the potential difference signal, the potential difference signal has reduced noise, and is in the state where a component related to cardiac action potential can be easily identified.

Incidentally, when a potential difference signal to be filtered by the amplifying unit 205 is a potential difference signal on a non-contact electrode, noise remains. For example, a potential difference signal on a non-contact electrode is a potential difference signal on a wheel electrode other than the wheel electrodes "3" and "9" on the time axis in FIG. 7. The potential difference signal does not include a component related to cardiac action potential in the first place; therefore, even after the potential difference signal is filtered, only noise remains.

Furthermore, the amplifying unit 205 changes an amplification factor to be applied to a potential difference signal in the various filtering processes. Specifically, the amplifying unit 205 receives information on "timing" to change an amplification factor used in the various filtering processes and an "instruction" on content of the change from a determining unit 403. Then, at the "timing" received from the determining unit 403, the amplifying unit 205 changes conditions used in the various filtering processes on the basis of the "instruction" received from the determining unit 403.

There is further explained taking for example a case where the wheel electrode "3" is contacted by the right hand. The amplifying unit 205 receives information on "timing" to receive a potential difference signal on the wheel electrode "3" from the determining unit 403. Furthermore, the amplifying unit 205 receives an "instruction" to amplify the potential difference signal using an amplification factor suitable for a combination of the right hand and the buttocks. Then, at the received "timing", the amplifying unit 205 changes an amplification factor used in the various filtering processes to a value suitable for the combination of the right hand and the buttocks.

In this manner, the amplifying unit 205 amplifies a potential difference signal by an amplification factor suitable for "a combination of two positions across the heart" corresponding to the received potential difference signal on the basis of the "timing" and "instruction" received from the determining unit 403. As a result, no matter which one of the plurality of wheel electrodes 201 is a contact electrode, no matter what "a combination of two positions across the heart" is, the amplifying unit 205 sends a potential difference signal that is easy for a beat identifying unit 404 to identify to the control unit 400.

To return to FIG. 2, the storage unit 300 is connected to the control unit 400, and stores therein data for various processes performed by the control unit 400. The storage unit 300 is, for example, a semiconductor memory device, such as a random access memory (RAM), a read-only memory (ROM), or a flash memory, or a storage device, such as a hard disk or an optical disk. In the example illustrated in FIG. 2, the storage unit 300 has a potential-difference storage unit 301 and a determination-result storage unit 302.

The potential-difference storage unit 301 stores therein a potential difference signal filtered by the amplifying unit 205. Here, an example of a potential difference signal stored in the potential-difference storage unit 301 is explained with reference to FIG. 9. FIG. 9 is a diagram for explaining about an example of information stored in a potential-difference storage unit in the second embodiment. Incidentally, in FIG. 9, the vertical axis indicates a potential difference, and the horizontal axis indicates the time axis.

A potential difference signal stored in the potential-difference storage unit 301 is a potential difference signal filtered by the amplifying unit 205. Therefore, as illustrated in (1) of FIG. 9, a potential difference signal on the wheel electrode 201 contacted by the driver has reduced noise, and is in the state where a component related to cardiac action potential can be easily identified. On the other hand, as illustrated in (2) of FIG. 9, a potential difference signal on a non-contact electrode does not include a component related to cardiac action potential in the first place, and is in a state where only noise is identified. Incidentally, information stored in the potential-difference storage unit 301 is stored by a potential-difference storing unit 401 of the control unit 400, and is used by an electrode identifying unit 402 of the control unit 400.

The determination-result storage unit 302 stores therein information indicating a combination of a result of determination by the determining unit 403 and identification information identifying a contact electrode which is an object of the determination result. An example of information stored in a determination-result storage unit in the second embodiment is explained with reference to FIG. 10. FIG. 10 is a diagram for explaining about an example of information stored in the determination-result storage unit in the second embodiment.

In the example illustrated in FIG. 10, the determination-result storage unit 302 stores therein information indicating a combination of identification information and a determination result in association with a time. For example, the determination-result storage unit 302 stores therein information indicating a combination of identification information "3" and a determination result "right hand" and information indicating a combination of identification information "9" and a determination result "left hand" in association with a time "10:10:10". The "time" illustrated in FIG. 10 denotes a time at which a determination process has been performed by the determining unit 403.

Namely, in the example illustrated in FIG. 10, the determination-result storage unit 302 stores therein a result of determination made at "10:10:10" by the determining unit 403. Specifically, the determination-result storage unit 302 stores therein a determination result indicating that the wheel electrode "3" is contacted by driver's right hand and a determination result indicating that the wheel electrode "9" is contacted by driver's left hand as a result of determination.

Incidentally, when driver's one hand is in contact with the wheel electrode 201, the determination-result storage unit 302 stores therein one combination of identification information and a determination result in association with a "time". In the example illustrated in FIG. 10, there is described a case where the determination-result storage unit 302 stores therein identification information indicating a contact electrode as identification information; however, the present embodiment is not limited to this case. For example, the determination-result storage unit 302 can store therein information indicating whether it is contacted by a driver or information indicating whether driver's hand is the right hand or the left hand with respect to each piece of identification information identifying a wheel electrode 201.

Furthermore, information stored in the determination-result storage unit 302 is input by the determining unit 403 each time the determining unit 403 performs a determination process. Namely, when the determining unit 403 performs a determination process, if the determining unit 403 has performed the determination process before, a result of previous determination has been stored in the determination-result storage unit 302.

To return to FIG. 2, the control unit 400 is connected to the amplifying unit 205 and the storage unit 300. The control unit 400 has an internal memory storing therein programs in which procedures of various processes are defined, and performs the various processes. The control unit 400 is, for example, an integrated circuit, such as an application specific integrated circuit (ASIC) or a field programmable gate array (FPGA), or an electronic circuit, such as a central processing unit (CPU) or a micro processing unit (MPU). In the example illustrated in FIG. 2, the control unit 400 has the potential-difference storing unit 401, the electrode identifying unit 402, the determining unit 403, and the beat identifying unit 404. The potential-difference storing unit 401 receives a potential difference signal from the amplifying unit 205, and stores the received potential difference signal in the potential-difference storage unit 301.

Figure 11A:
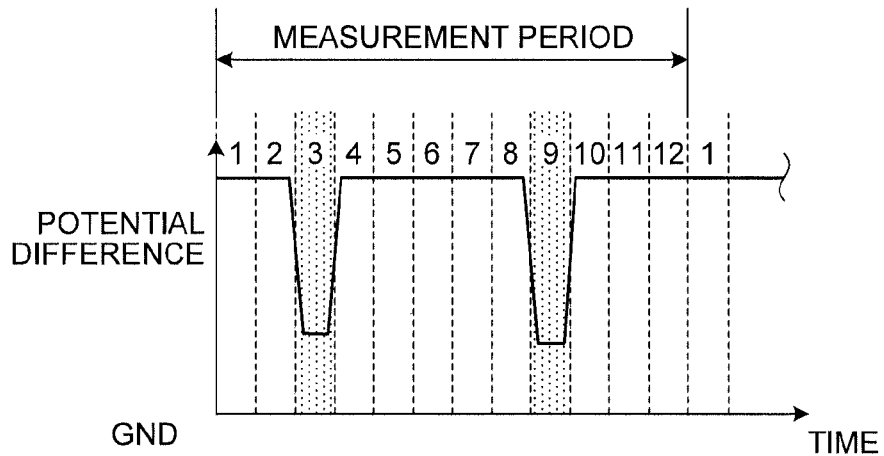
FIG. 11A is a diagram for explaining about a process to identify a contact electrode.
Figure 11B:
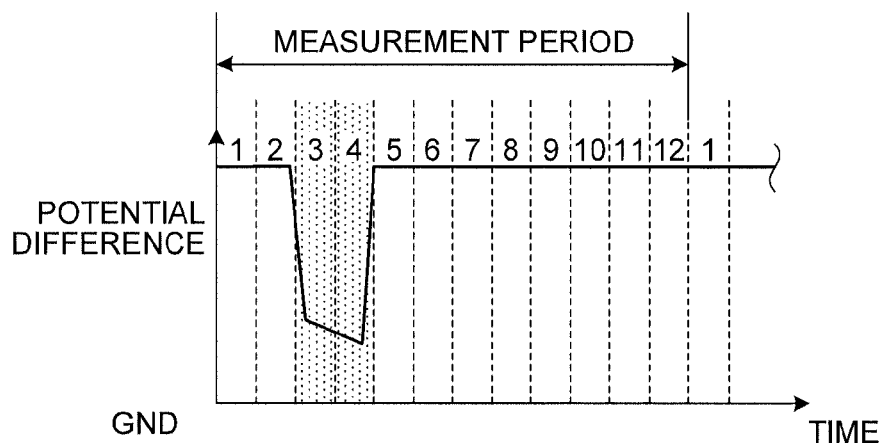
FIG. 11B is a diagram for explaining about the process to identify a contact electrode.
Figure 11C:
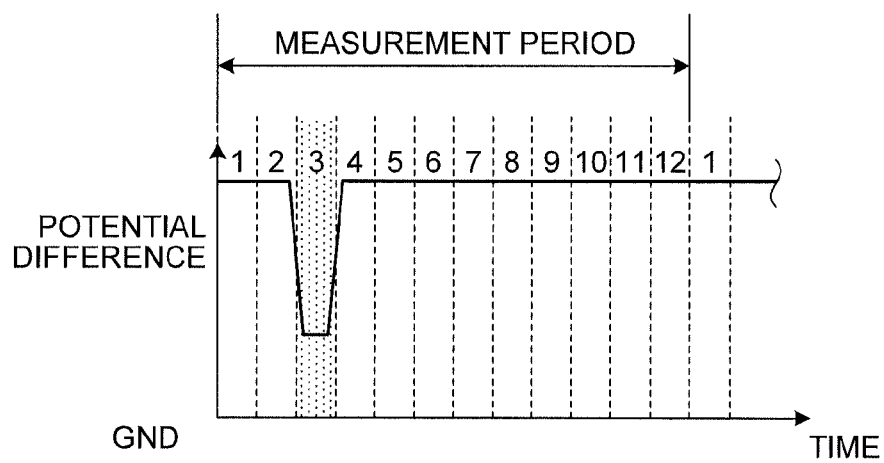
FIG. 11C is a diagram for explaining about the process to identify a contact electrode.

The electrode identifying unit 402 acquires a potential difference signal stored in the potential-difference storage unit 301, and identifies a contact electrode contacted by driver's hand out of the plurality of wheel electrodes 201. A contact-electrode identifying process performed by an electrode identifying unit in the second embodiment is explained with reference to FIGS. 11A to 11C. FIGS. 11A to 11C are diagrams for explaining about a process to identify a contact electrode. Incidentally, in FIGS. 11A to 11C, the vertical axis indicates a potential difference, and the horizontal axis indicates the time axis.

For example, the electrode identifying unit 402 identifies a point having a smaller potential difference than other points out of received potential difference signals, and identifies that the wheel electrode 201 corresponding to the identified point is a contact electrode. In an example illustrated in FIG. 11A, there are two points having a small potential difference within the measurement period, and the electrode identifying unit 402 identifies that the points corresponding to the wheel electrodes "3" and "9" are small in potential difference. As a result, the electrode identifying unit 402 identifies that the wheel electrodes "3" and "9" are contact electrodes.

In an example illustrated in FIG. 11B, there is one point having a small potential difference within the measurement period; however, the width of the point having a small potential difference is long, and the electrode identifying unit 402 identifies that potential differences on the wheel electrodes "3" and "4" are small. As a result, the electrode identifying unit 402 identifies that the wheel electrodes "3" and "4" are contact electrodes.

In an example illustrated in FIG. 11C, there is one point having a small potential difference within the measurement period, and the electrode identifying unit 402 identifies that the point corresponding to the wheel electrode "3" is small in potential difference. As a result, the electrode identifying unit 402 identifies that the wheel electrode "3" is a contact electrode.

For example, the electrode identifying unit 402 measures an average potential difference at intervals of the measurement period, and identifies a point indicating a smaller potential difference than the measured average potential difference as a point having a small potential difference. Furthermore, for example, when a threshold value for distinguishing between a point which is small in potential difference and a point which is not small is set by a user in advance, the electrode identifying unit 402 can identify a point having a small potential difference using the set threshold value.

Furthermore, the electrode identifying unit 402 identifies a contact electrode, thereby identifying whether the wheel electrode(s) 201 is contacted by driver's both hands or one hand. When identifying two contact electrodes as illustrated in FIGS. 11A and 11B, the electrode identifying unit 402 identifies that the wheel electrodes 201 are contacted by driver's both hands. Furthermore, when identifying one contact electrode as illustrated in FIG. 11C, the electrode identifying unit 402 identifies that the wheel electrode 201 is contacted by driver's one hand.

Moreover, the electrode identifying unit 402 identifies a contact electrode at intervals of the measurement period, and sends a result of the identification to the determining unit 403. For example, the electrode identifying unit 402 sends information that contact electrodes are the wheel electrodes "3"

and "9" and the wheel electrodes 201 are contacted by "both hands" of the driver to the determining unit 403.

To return to FIG. 2, the determining unit 403 is connected to the selection circuit 203, the amplifying unit 205, the determination-result storage unit 302, and the electrode identifying unit 402. Furthermore, although not illustrated in FIG. 2, the determining unit 403 is connected to a control device of the vehicle. The determining unit 403 receives a result of identification from the electrode identifying unit 402, and acquires a rotational state of the steering wheel 501 from the control device of the vehicle.

In a case where it is the first time to perform a determination process, the determining unit 403 determines whether the driver's hand by which the contact electrode is contacted is the right hand or the left hand on the basis of the rotational state of the steering wheel 501 and the identification result actually received from the electrode identifying unit 402. The identification result actually received from the electrode identifying unit 402 is, in other words, the current identification result. Furthermore, except when it is the first time to perform a determination process, the determining unit 403 determines whether driver's hand by which a contact electrode is contacted is the right hand or the left hand on the basis of a previous determination result stored in the determination-result storage unit 302 and the current identification result.

Incidentally, "when it is the first time to perform a determination process" means at the time of first processing and when no previous determination result is stored in the determination-result storage unit 302. Furthermore, "when no previous determination result is stored in the determination-result storage unit 302" means when there is no result of determination previously performed in a predetermined time frame at the time for the determining unit 403 to make a determination.

Moreover, "when it is the first time to perform a determination process" includes when a previous determination result does not correspond to the current identification result. For example, "when it is the first time to perform a determination process" also includes when while the current contact electrodes are the wheel electrodes "3" and "9", the determination-result storage unit 302 does not store therein determination results indicating the contact electrodes "3" and "9" in association with the latest time.

The process for the determining unit 403 to determine whether driver's hand is the right hand or the left hand is explained in more detail. The determining unit 403 identifies which one of the following five cases is met using the current identification result and a previous determination result. Then, the determining unit 403 performs a determination process corresponding to the identified case.

"Case 1" is a case where the current identification result indicates "contact by both hands" and there is "no" previous determination result stored.

"Case 2" is a case where the current identification result indicates "contact by both hands" and the previous determination result indicates "contact by both hands".

"Case 3" is a case where the current identification result indicates "contact by both hands" and the previous determination result indicates "contact by one hand".

"Case 4" is a case where the current identification result indicates "contact by one hand" and there is "no" previous determination result stored.

"Case 5" is a case where the current identification result indicates "contact by one hand" and the previous determination result indicates "contact by both hands" or "contact by one hand".

Respective determination processes performed by the determining unit 403 in the above "Case 1" to "Case 5" are explained below. Incidentally, the "Case 1" and the "Case 4" are the case where there is "no" previous determination result stored, and correspond to "when it is the first time to perform a determination process". Furthermore, the "Case 2", the "Case 3", and the "Case 5" are the case where there is a previous determination result stored, and correspond to "except when it is the first time to perform a determination process".

Determination Process in Case 1

First, a determination process in the "Case 1" is explained. The determining unit 403 determines whether driver's hand in contact with a contact electrode is the right hand or the left hand on the basis of a rotational state of the steering wheel 501 and the current identification result. Specifically, the determining unit 403 determines that the hand in contact with a contact electrode on the right side from the driver is the right hand. Furthermore, the determining unit 403 determines that the hand in contact with a contact electrode on the left side from the driver is the left hand. Namely, in the "Case 1", the previous determination result is not used at all, so the determining unit 1403 determines whether driver's hand in contact with a contact electrode is the right hand or the left hand anew.

Here, the "Case 1" is explained taking for example a case where the current contact electrodes are the wheel electrodes "3" and "9". In this case, the determining unit 403 identifies whether the contact electrode "3" or "9" is on the left side or the right side of the driver using a rotational state of the steering wheel 501. Then, when the contact electrode "3" is on the right side of the driver and the contact electrode "9" is on the left side of the driver, the determining unit 403 determines that the wheel electrode "3" is contacted by driver's right hand and the wheel electrode "9" is contacted by driver's left hand. Incidentally, details of the process of determination using a rotational state of the steering wheel 501 will be described later, so detailed description of the process is omitted here.

Determination Process in Case 2

Subsequently, a determination process in the "Case 2" is explained. The determining unit 403 acquires a previous determination result from the determination-result storage unit 302, and takes the acquired previous determination result as a determination result. Namely, in the "Case 2", the previous determination result and the current identification result both indicate contact by driver's both hands, and the determining unit 403 determines that the same contact has been made continuously from the previous time.

Here, the "Case 2" is explained taking for example a case where the current contact electrodes are the wheel electrodes "3" and "9". Furthermore, there is explained under the assumption that the previous determination result is information indicating a combination of identification information "3" and a determination result "right hand" and information indicating identification information "9" and a determination result "left hand". In this case, the determining unit 403 determines that the wheel electrode "3" is contacted by driver's right hand and the wheel electrode "9" is contacted by driver's left hand.

Determination Process in Case 3

Subsequently, a determination process in the "Case 3" is explained. The determining unit 403 acquires a previous determination result from the determination-result storage unit 302. Then, the determining unit 403 first uses the acquired previous determination result as a determination result. After that, the determining unit 403 determines that hand in contact with the remaining contact electrode is the remaining hand. Namely, in the "Case 3", as for a common contact electrode with the previous determination result out of the current two contact electrodes, the determining unit 403 determines that the same contact has been made continuously from the previous time. Then, as for the other contact electrode which is not a common contact electrode with the previous determination result, the determining unit 403 determines that the contact electrode is contacted by driver's hand which has had no contact with any contact electrode in the previous time.

Here, the "Case 3" is explained taking for example a case where the current contact electrodes are the wheel electrodes "3" and "9". Furthermore, there is explained under the assumption that the previous determination result is information indicating a combination of identification information "3" and a determination result "right hand". In this case, the determining unit 403 first determines that the wheel electrode "3" is contacted by driver's right hand. After that, the determining unit 403 determines that the remaining contact electrode, i.e., the wheel electrode "9" is contacted by the remaining hand, i.e., driver's "left hand".

Determination Process in Case 4

Subsequently, a determination process in the "Case 4" is explained. The determining unit 403 determines whether driver's hand in contact with a contact electrode is the right hand or the left hand on the basis of a rotational state of the steering wheel 501 and the current identification result. Specifically, if the contact electrode is on the right side of the driver, the determining unit 403 determines that the hand in contact with the contact electrode is the right hand; on the other hand, if the contact electrode is on the left side of the driver, the determining unit 403 determines that the hand in contact with the contact electrode is the left hand. Namely, in the "Case 4", the previous determination result is not used at all, so the determining unit 403 determines whether driver's hand in contact with a contact electrode is the right hand or the left hand anew in the same manner as in the "Case 1".

Here, the "Case 4" is explained taking for example a case where the current contact electrode is the wheel electrode "3". In this case, the determining unit 403 identifies whether the contact electrode "3" is on the left side or the right side of the driver using a rotational state of the steering wheel 501. Then, when the contact electrode "3" is on the right side of the driver, the determining unit 403 determines that the wheel electrode "3" is contacted by driver's right hand. On the other hand, when the contact electrode "3" is on the left side of the driver, the determining unit 403 determines that the wheel electrode "3" is contacted by driver's left hand. Incidentally, details of the process of determination using a rotational state of the steering wheel 501 will be described later, so detailed description of the process is omitted here.

Determination Process in Case 5

Subsequently, a determination process in the "Case 5" is explained. The determining unit 403 acquires a previous determination result corresponding to the current contact electrode from the determination-result storage unit 302. Then, the determining unit 403 takes the acquired previous determination result as a determination result. Namely, as for the current contact electrode common with the previous determination result, the determining unit 403 determines that the same contact has been made continuously from the previous time.

Here, the "Case 5" is explained taking for example a case where the current contact electrode is the wheel electrode "3". Furthermore, there is explained under the assumption that the previous determination result is information indicating a combination of identification information "3" and a determination result "right hand". In this case, the determining unit 403 determines that the wheel electrode "3" is contacted by driver's right hand.

About Determining Unit Taking Rotational State of Wheel into Account

Figure 12A:
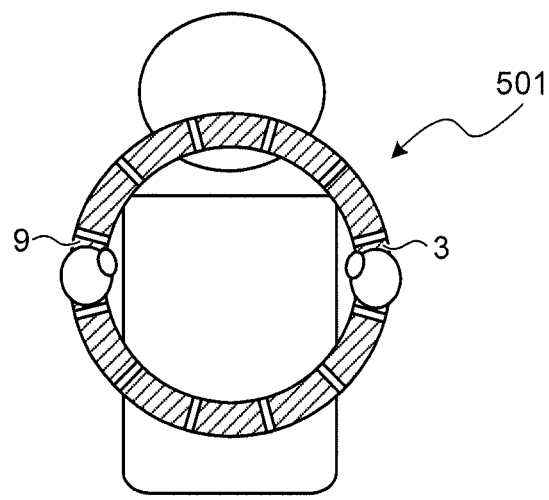
FIG. 12A is a diagram for explaining about a relation between a rotational state of a wheel and positions of wheel electrodes.
Figure 12B:
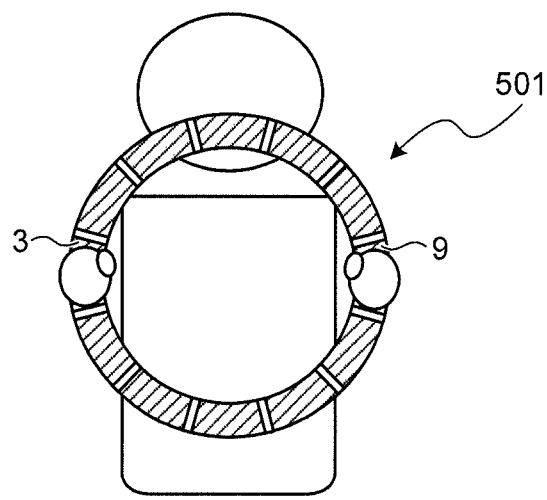
FIG. 12B is a diagram for explaining about the relation between a rotational state of the wheel and position of the wheel electrodes.

As described above, in the "Case 1" and the "Case 4", the determining unit 403 identifies whether a contact electrode is on the left side or the right side of the driver using a rotational state of the steering wheel 501. Here, the reason why the determining unit 403 takes a rotational state of the steering wheel 501 into account is explained with reference to FIGS. 12A and 12B. FIGS. 12A and 12B are diagrams for explaining about a relation between a rotational state of a wheel and positions of wheel electrodes. FIGS. 12A and 12B illustrate an example of the steering wheel 501 held by the driver; in the example, the steering wheel 501 is on the front side, and the driver is located behind the steering wheel 501.

Here, the wheel electrode "3" may be on the left side of the driver and the wheel electrode "9" may be on the right side of the driver as illustrated in FIG. 12A, or the wheel electrode "9" may be on the left side of the driver and the wheel electrode "3" may be on the right side of the driver as illustrated in FIG. 12B. Namely, the steering wheel 501 is rotated, so even when it is found that contact electrodes are the wheel electrodes "3" and "9", the determining unit 403 does not identify which one of the contact electrodes is on the right side or left side of the driver.

Therefore, the determining unit 403 acquires a rotation angle of the steering wheel 501 rotated to the right (or the left) by the driver, for example, based on a position of the wheel when the vehicle goes straight ahead. Then, the determining unit 403 determines that either one of the two contact electrodes located on the right side than the other is on the right side of the driver, and determines that either one of the two contact electrodes located on the left side than the other is on the left side of the driver.

In an example illustrated in FIG. 12B, the determining unit 403 identifies that the wheel electrode "9" is on the left side than the wheel electrode "3" from a rotation angle of the steering wheel 501. As a result, the determining unit 403 determines that driver's hand in contact with the wheel electrode "9" is the left hand. Furthermore, the determining unit 403 identifies that the wheel electrode "3" is on the right side than the wheel electrode "9" from the rotation angle. As a result, the determining unit 403 determines that driver's hand in contact with the wheel electrode "3" is the right hand.

Example of Determination Process Performed by Determining Unit

Figure 13:
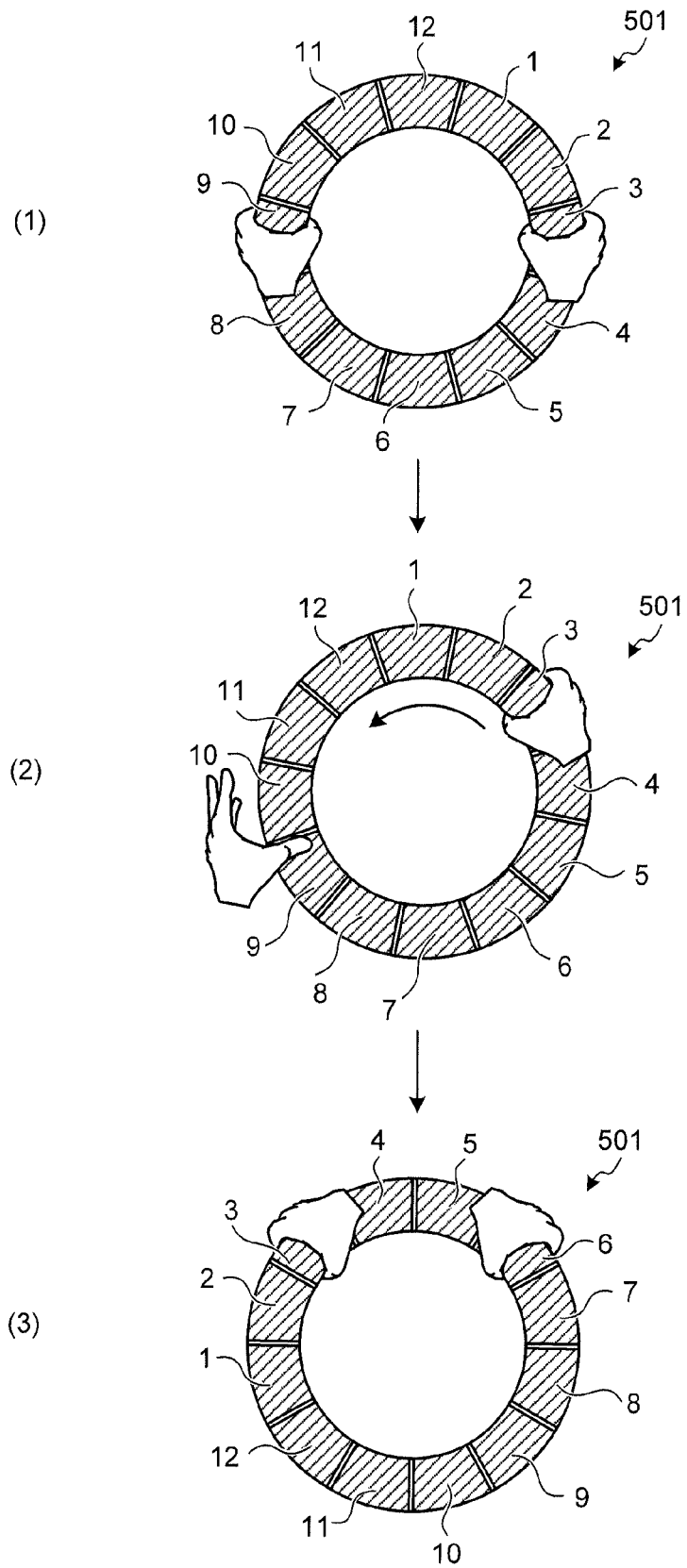
FIG. 13 is a diagram for explaining about a process performed by a determining unit in the second embodiment.

Here, an example of a determination process performed by the determining unit 403 is further explained with reference to FIG. 13. FIG. 13 is a diagram for explaining about a process performed by a determining unit in the second embodiment. In (1) to (3) of FIG. 13, there is illustrated for example a case where twelve uniformly-sized wheel electrodes 201 are installed along a circumferential direction of the steering wheel 501. Furthermore, (1) to (3) of FIG. 13 indicate an example of a relation between the steering wheel 501 and driver's hands when the driver steers to the left.

First, as illustrated in (1) of FIG. 13, the driver is holding the steering wheel 501 with both hands. As a result, the determination-result storage unit 302 has stored therein information indicating a combination of identification information "3" and a determination result "right hand" and information indicating a combination of identification information "9" and a determination result "left hand" as a previous determination result.

After that, as illustrated in (2) of FIG. 13, the driver begins to steer to the left, and releases the left hand from the steering wheel 501. At this point, the determining unit 403 determines that it is not the first determination process, and reads out a previous determination result associated with identification information identifying the contact electrode "3" from the determination-result storage unit 302. For example, the determining unit 403 reads out information indicating a combination of identification information "3" and a determination result "right hand". As a result, the determining unit 403 determines that the wheel electrode "3" is contacted by driver's right hand.

Then, as illustrated in (3) of FIG. 13, the driver further steers to the left, and the wheel electrode "6" on the left side of the driver is contacted by the left hand. At this point, the determining unit 403 determines that it is not the first determination process, and reads out a previous determination result associated with identification information identifying the contact electrode "3" or "6". For example, the determining unit 403 reads out information indicating a combination of identification information "3" and a determination result "right hand". As a result, the determining unit 403 first determines that the wheel electrode "3" is contacted by driver's right hand, and then determines that the remaining contact electrode, i.e., the wheel electrode "6" is contacted by the remaining hand, i.e., driver's "left hand".

Process After Determination Made by Determining Unit

Subsequently, a process performed after the determination is made by the determining unit 403 is explained. The determining unit 403 stores a result of the determination in the determination-result storage unit 302. There is further explained taking for example a case where the determining unit 403 has determined that driver's hand in contact with the wheel electrode "9" is the left hand and driver's hand in contact with the wheel electrode "3" is the right hand. In this case, the determining unit 403 stores a combination of identification information "3" and a determination result "right hand" and a combination of identification information "9" and a determination result "left hand" in association with a current time in the determination-result storage unit 302.

Furthermore, the determining unit 403 sends information on "timing" and an "instruction" to the amplifying unit 205 on the basis of the determination result. As a result, the determining unit 403 causes the amplifying unit 205 to amplify a potential difference signal by an amplification factor determined on the basis of the determination result.

There is further explained taking for example a case where the determining unit 403 has determined that driver's hand in contact with the wheel electrode "9" is the right hand and driver's hand in contact with the wheel electrode "3" is the left hand. In this case, the determining unit 403 sends an instruction to amplify a potential difference signal on the wheel electrode "9" by an amplification factor suitable for a combination of the right hand and the buttocks to the amplifying unit 205. Furthermore, the determining unit 403 sends the timing for the amplifying unit 205 to receive the potential difference signal on the wheel electrode "9". Moreover, for example, the determining unit 403 sends an instruction to amplify a potential difference signal on the wheel electrode "3" by an amplification factor suitable for a combination of the left hand and the buttocks to the amplifying unit 205. In addition, the determining unit 403 sends the timing for the amplifying unit 205 to receive the potential difference signal on the wheel electrode "3".

Namely, on the basis of facts that the heart is located at a position slightly deviated from the center of body and consequently the intensity of a heart rate signal differs according to a combination of two positions across the heart, the determining unit 403 sends an instruction to amplify a potential difference signal by an amplification factor suitable for a combination of two positions. For example, as for a potential difference signal on the wheel electrode 201 contacted by the right hand, an instruction to use an amplification factor suitable for the intensity of a heart rate signal included in a measured potential difference between the buttocks and the right hand is sent.

Furthermore, for example, a potential difference signal measured by using a combination of the right hand and the seat includes a stronger heart rate signal than that is included in a potential difference signal measured by using a combination of the left hand and the seat. Therefore, the determining unit 403 sends an instruction to use, with respect to a potential difference signal on the wheel electrode 201 contacted by the left hand, a higher amplification factor than that is used with respect to a potential difference signal on the wheel electrode 201 contacted by the right hand.

To return to the explanation of FIG. 2, the beat identifying unit 404 acquires a potential difference signal stored in the potential-difference storage unit 301, and identifies a component related to cardiac action potential from the acquired potential difference signal. Namely, the beat identifying unit 404 identifies the heart beat. As described above, the amplifying unit 205 amplifies a potential difference signal by an amplification factor based on an instruction issued by the determining unit 403. Consequently, the potential-difference storage unit 301 stores therein the potential difference signal amplified on the basis of the instruction issued by the determining unit 403. Therefore, the beat identifying unit 404 identifies the heart beat from the potential difference signal amplified on the basis of the instruction issued by the determining unit 403.

A processes to identify the heart beat in a case where the wheel electrodes 201 are contacted by driver's both hands and a processes to identify the heart beat in a case where the wheel electrode 201 is contacted by driver's one hand are further explained.

First, the process in the case where the wheel electrodes 201 are contacted by driver's both hands is explained. The beat identifying unit 404 subtracts a potential difference signal on the wheel electrode 201 contacted by the driver's left hand from a potential difference signal on the wheel electrode 201 contacted by the driver's right hand, thereby measuring a potential difference signal corresponding to a combination of the right hand and the left hand. For example, the beat identifying unit 404 acquires a potential difference signal on the wheel electrode 201 contacted by the driver's right hand out of potential difference signals stored in the potential-difference storage unit 301, and further acquires a potential difference signal on the wheel electrode 201 contacted by the driver's left hand. Then, the beat identifying unit 404 performs subtraction using the acquired potential difference signals, thereby measuring a potential difference signal corresponding to a combination of the right hand and the left hand. Then, the beat identifying unit 404 identifies the heart beat from the potential difference signal corresponding to the combination of the right hand and the left hand.

Incidentally, the measurement can be made by subtracting a potential difference signal on the wheel electrode 201 contacted by the driver's right hand from a potential difference signal on the wheel electrode 201 contacted by the driver's left hand. In the case of using the potential difference signal corresponding to the combination of the right hand and the left hand, noise can be further reduced as compared with a case of using a potential difference signal corresponding to a combination of the right hand and the seat or a combination of the left hand and the seat, and therefore the beat identifying unit 404 can identify cardiac action potential more definitely.

The process in the case where the wheel electrode 201 is contacted by driver's one hand is explained. The beat identifying unit 404 acquires a potential difference signal on the wheel electrode 201 contacted by the driver's hand, and identifies the heart beat from the acquired potential difference signal. For example, when the contact electrode is the wheel electrode "3", the beat identifying unit 404 acquires a potential difference signal on the wheel electrode "3", and identifies the heart beat.

In this manner, when it is possible to measure a wheel potential difference signal which is a potential difference signal between two contact electrodes contacted by a driver out of a plurality of electrodes installed in the steering wheel 501 of the vehicle, the determining unit 403 identifies a heart rate signal using the wheel potential difference signal. On the other hand, when it is not possible to measure a wheel potential difference signal, the determining unit 403 identifies a heart rate signal using a potential difference signal between one contact electrode out of the plurality of electrodes installed in the steering wheel 501 of the vehicle and a different contact electrode from the electrodes installed in the wheel.

Incidentally, the beat identifying unit 404 identifies whether the wheel is contacted by driver's both hands or one hand using a potential difference signal stored in the potential-difference storage unit 301. For example, when there are two points having a small potential difference every measurement period as illustrated in FIG. 11A or 11B, the beat identifying unit 404 identifies that the wheel is contacted with both hands. Furthermore, for example, when there is one point having a small potential difference every measurement period as illustrated in FIG. 11C, the beat identifying unit 404 identifies that the wheel is contacted with one hand. Incidentally, the beat identifying unit 404 can identify whether the wheel is contacted with driver's both hands or one hand upon receipt of a determination result from the determining unit 403.

Process Performed by Identification Device

Figure 14:
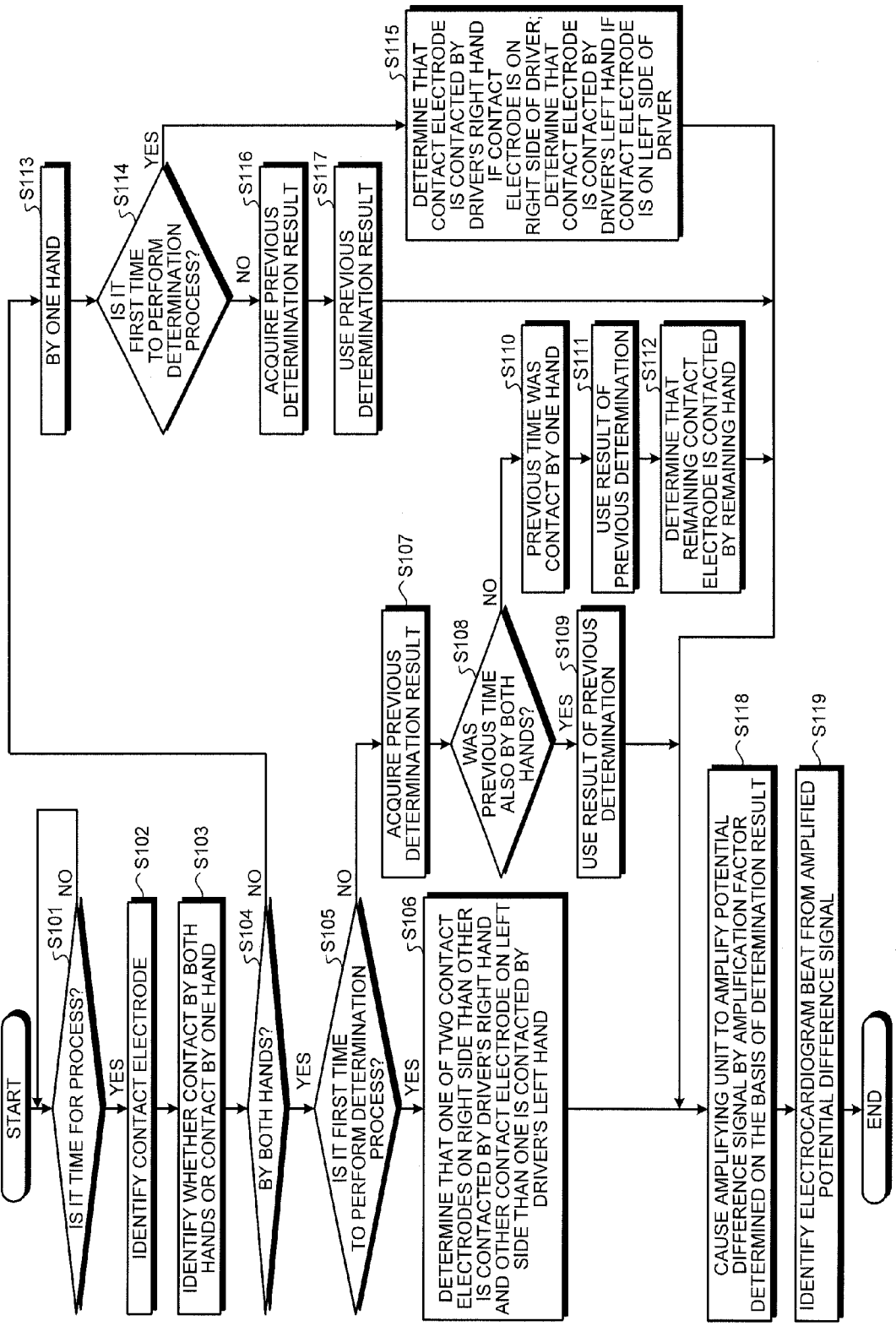
FIG. 14 is a flowchart for explaining about an example of the flow of a process performed by a control unit in the second embodiment.

Subsequently, an example of the flow of a process performed by the control unit 400 in the second embodiment is explained with reference to FIG. 14. FIG. 14 is a flowchart for explaining about an example of the flow of the process performed by the control unit 400 in the second embodiment.

As illustrated in FIG. 14, when it comes to a time for the process (YES at S101), the electrode identifying unit 402 identifies a contact electrode contacted by driver's hand out of a plurality of electrodes installed in the steering wheel 501 (S102). For example, the electrode identifying unit 402 identifies that contact electrodes are the wheel electrodes "3" and "9".

Then, the electrode identifying unit 402 identifies whether contact by both hands or contact by one hand (S103). For example, when identifying two contact electrodes, the electrode identifying unit 402 identifies that the wheel electrodes 201 are contacted by driver's both hands. Furthermore, for example, when identifying one contact electrode, the electrode identifying unit 402 identifies that the wheel electrode 201 is contacted by driver's one hand.

Here, there is explained a case where contact by driver's both hands is identified by the electrode identifying unit 402 (YES at S104). The determining unit 403 determines whether it is the first time to perform a determination process (S105). Then, when determining that it is the first time (YES at S105), the determining unit 403 determines that one of the two contact electrodes on the right side than the other is contacted by driver's right hand and the other contact electrode on the left side than the one is contacted by driver's left hand (S106).

Furthermore, at S105, when determining that it is not the first time (NO at S105), the determining unit 403 acquires a previous determination result out of determination results stored in the determination-result storage unit 302 (S107). Here, if the previous determination result indicates contact by both hands (YES at S108), the determining unit 403 uses the acquired determination result as-is (S109). There is explained a case where the determining unit 403 has acquired, for example, information indicating a combination of identification information "3" and a determination result "right hand" and information indicating a combination of identification information "9" and a determination result "left hand". In this case, the determining unit 403 determines that the wheel electrode "3" is contacted by the driver's right hand and the wheel electrode "9" is contacted by the driver's left hand.

On the other hand, when the previous determination result does not indicate contact by both hands (NO at S108), i.e., when the previous determination result indicates contact by one hand (S110), the determining unit 403 first uses the acquired determination result (S111). For example, when the determining unit 403 has acquired information indicating a combination of identification information "3" and a determination result "right hand", the determining unit 403 determines that the wheel electrode "3" is contacted by the driver's right hand. Then, the determining unit 403 determines that the remaining contact electrode is contacted by the remaining hand (S112). For example, the determining unit 403 determines that the remaining contact electrode, i.e., the wheel electrode "9" is contacted by the remaining hand, i.e., driver's "left hand".

Furthermore, there is explained a case where at S104, the electrode identifying unit 402 identifies not contact by driver's both hands (NO at S104) but contact by driver's one hand (S113).

Here, the determining unit 403 determines whether it is the first time to perform a determination process (S114). Then, when determining that it is the first time (YES at S114), the determining unit 403 determines that a contact electrode is contacted by driver's right hand if the contact electrode is on the right side of the driver. Furthermore, if a contact electrode is on the left side of the driver, the determining unit 403 determines that the contact electrode is contacted by driver's left hand (S115).

On the other hand, at S114, when determining that it is not the first time (NO at S114), the determining unit 403 acquires a previous determination result (S116), and uses the previous determination result (S117).

After that, the determining unit 403 causes the amplifying unit 205 to amplify a potential difference signal measured by the potential-difference measuring unit 204 using an amplification factor determined on the basis of the determination result (S118). Then, the beat identifying unit 404 identifies the heart beat from the potential difference signal amplified by the amplifying unit 205 (S119).

Incidentally, the flow of the process described above is not limited to the flow illustrated in FIG. 14. For example, all of the above-described process does not have to be performed in series. For example, the identification device 200 performs the processes at S101 to S118 in series, and causes the amplifying unit 205 to amplify a potential difference signal by an amplification factor determined on the basis of a determination result. Then, the identification device 200 can identify the heart beat from the potential difference signal at the different timing from the timing to perform the amplification process.

Effects of Second Embodiment

As described above, according to the second embodiment, the identification device 200 measures a potential difference signal between one contact electrode out of the plurality of wheel electrodes 201 and the seat electrode 202 different from the electrodes installed in the steering wheel 501. Then, the identification device 200 identifies a contact electrode contacted by driver's hand out of the plurality of wheel electrodes 201, and determines whether the driver's hand in contact with the contact electrode is the right hand or the left hand on the basis of a position of the contact electrode in the wheel and a rotational state of the wheel. Then, the identification device 200 identifies the heart beat from the potential difference signal amplified by an amplification factor determined on the basis of the determination result. Consequently, it is possible to distinguish whether driver's hand in contact with the wheel electrode 201 installed in the steering wheel 501 is the right hand or the left hand. Furthermore, whether the hand in contact with the electrode on the wheel is the right hand or the left hand can be determined, and as a result, it is possible to identify the heart beat using an amplification factor suitable for a combination of two positions of electrodes between which a potential difference signal is measured, and also possible to identify a weak heart rate signal which is apt to be buried in noise with a high degree of accuracy. Furthermore, no matter whether the hand in contact with the wheel electrode 201 is the right hand or the left hand, or even both hands, a heart rate signal can be detected with accuracy; therefore, it is possible to increase a duration of detection of a heart rate signal.

For example, if the amplifying unit 205 continues to apply the same amplification factor, when the combination of two positions across the heart is switched, a component related to cardiac action potential is likely to be buried in noise. There is further explained taking for example a case where the combination of two positions is switched, and as a result, a component related to cardiac action potential becomes weaker than it is before switching of the combination of two positions. In this case, the component related to cardiac action potential is weaker than it is before switching of the combination of two positions, and consequently the component related to cardiac action potential is likely to be buried in noise. However, according to the second embodiment, the identification device 200 can identify the heart beat using an amplification factor suitable for a combination of two positions of electrodes between which a potential difference signal is measured; therefore, even if the combination of two positions is switched, the identification device 200 can identify a weak heart rate signal which is apt to be buried in noise with a high degree of accuracy.

Furthermore, according to the second embodiment, the identification device 200 further includes the determination-result storage unit 302 that stores therein a result of determination by the determining unit 403 and identification information identifying a contact electrode which is an object of the determination result in an associated manner. Then, the identification device 200 identifies a contact electrode, thereby identifying whether driver's both hands or one hand is in contact with the wheel electrode 201. Then, when identifying contact by driver's one hand of, the identification device 200 reads out a previous determination result by referring to the determination-result storage unit 302, and, if the read previous determination result indicates that the contact electrode is contacted by the right hand, determines that the contact electrode is contacted by the right hand. Furthermore, similarly, if the read previous determination result indicates that the contact electrode is contacted by the left hand, the identification device 200 determines that the contact electrode is contacted by the left hand. As a result, if it is not the first process, it is possible to continuously distinguish whether driver's hand by which the wheel electrode 201 installed in the steering wheel 501 is contacted is the right hand or the left hand. For example, even if the driver steers and a position of the hand in contact with the wheel electrode 201 is changed, whether the hand by which the wheel electrode 201 is contacted is the right hand or the left hand can be distinguished.

Moreover, according to the second embodiment, when the wheel electrodes 201 are contacted by driver's both hands, the beat identifying unit 404 identifies a heart rate signal using a wheel potential difference signal. Furthermore, when the wheel electrode 201 is contacted by driver's one hand, the beat identifying unit 404 identifies a heart rate signal using a potential difference signal between the one contact electrode out of the wheel electrodes 201 and the seat electrode 202. As a result, no matter whether the wheel electrode 201 is contacted by driver's both hands or one hand, the heart beat can be continuously identified.

[c] Third Embodiment

The other embodiments are explained below.

Electrode

For example, in the above embodiment, there is described the case where an electrode installed in the seat 502 of the vehicle is used as a different electrode from electrodes installed in the steering wheel 501; however, the present embodiment is not limited to this case, and, for example, an electrode can be installed in a seat belt of the vehicle and used instead of the electrode installed in the seat 502.

Furthermore, in the above embodiment, there is described the case where driver's hand is in contact with one wheel electrode 201 at a time; however, the present embodiment is not limited to this case. Specifically, driver's hand can be in contact with a plurality of wheel electrodes 201 at a time. Namely, for example, each wheel electrode, such as the wheel electrode "1" or "2", can be divided into a plurality of electrodes.

Wheel Potential Difference Signal

Moreover, in the above embodiment, there is described the case where the beat identifying unit 404 measures a wheel potential difference signal using a potential difference signal stored in the potential-difference storage unit 301; however, the present embodiment is not limited to this case. For example, the potential-difference measuring unit 204 can measure a wheel potential difference signal.

For example, the selection circuit 203 selects two wheel electrodes 201 as detection sources of electric potential to be sent to the potential-difference measuring unit 204, and sends respective electric potentials detected by the selected two wheel electrodes 201. Furthermore, the selection circuit 203 changes a combination of the two wheel electrodes 201 on a regular basis. Then, the potential-difference measuring unit 204 measures a difference between the two electric potentials received from the selection circuit 203. As a result, when the wheel electrodes 201 are contacted by driver's both hands, the potential-difference measuring unit 204 measures a wheel potential difference signal.

After that, when the wheel potential difference signal has been stored in the potential-difference storage unit 301, the beat identifying unit 404 identifies the heart beat from the wheel potential difference signal. Namely, the beat identifying unit 404 identifies whether any of potential difference signals corresponding to a combination of the two wheel electrodes 201 out of potential difference signals stored in the potential-difference storage unit 301 is a potential difference signal including the heart beat. Then, when identifying that there is a potential difference signal including the heart beat, the beat identifying unit 404 identifies the heart beat from the identified potential difference signal. On the other hand, when no wheel potential difference signal is stored in the potential-difference storage unit 301, the beat identifying unit 404 identifies the heart beat from a potential difference signal between driver's one hand and the seat.

System Configuration

Furthermore, out of the processes described in the present embodiments, all or part of the process described as the one that is automatically performed can be manually performed. For example, the heart beat can be manually identified from a potential difference signal. In addition, the control procedures, specific names, and information including various data and parameters illustrated in the above description and the drawings (for example, FIGS. 1 to 14) can be arbitrarily changed unless otherwise specified.

Moreover, the elements of the devices illustrated in the drawings are functionally conceptual ones, and do not always have to be physically configured as illustrated in the drawings. Namely, specific forms of dispersion and integration of the elements in the devices are not limited to those illustrated in the drawings, and all or part of the elements can be configured to be functionally or physically dispersed or integrated in arbitrary units depending on respective loads or usages, etc. For example, the wheel electrodes 201 and the seat electrodes 202 can be configured as an external device of the identification device 200 and connected to the identification device 200 via a network (such as a wireless LAN (Local Area Network)). Furthermore, the above-described functions of the identification device 200 can be implemented in such a way that other devices have the potential-difference storage unit 301 and the determination-result storage unit 302, respectively, and the other devices are connected to the identification device 200 via a network and work in cooperation with the identification device 200.

Computer

Furthermore, the various processes described in the above embodiments can be realized by causing a computer, such as a personal computer or a workstation, to execute a program prepared in advance. An example of the computer that executes an identification program having the same functions as those described in the above embodiments is explained below. Incidentally, FIG. 15 is a diagram for explaining an example of a computer that executes an identification program according to the second embodiment.

Figure 15:
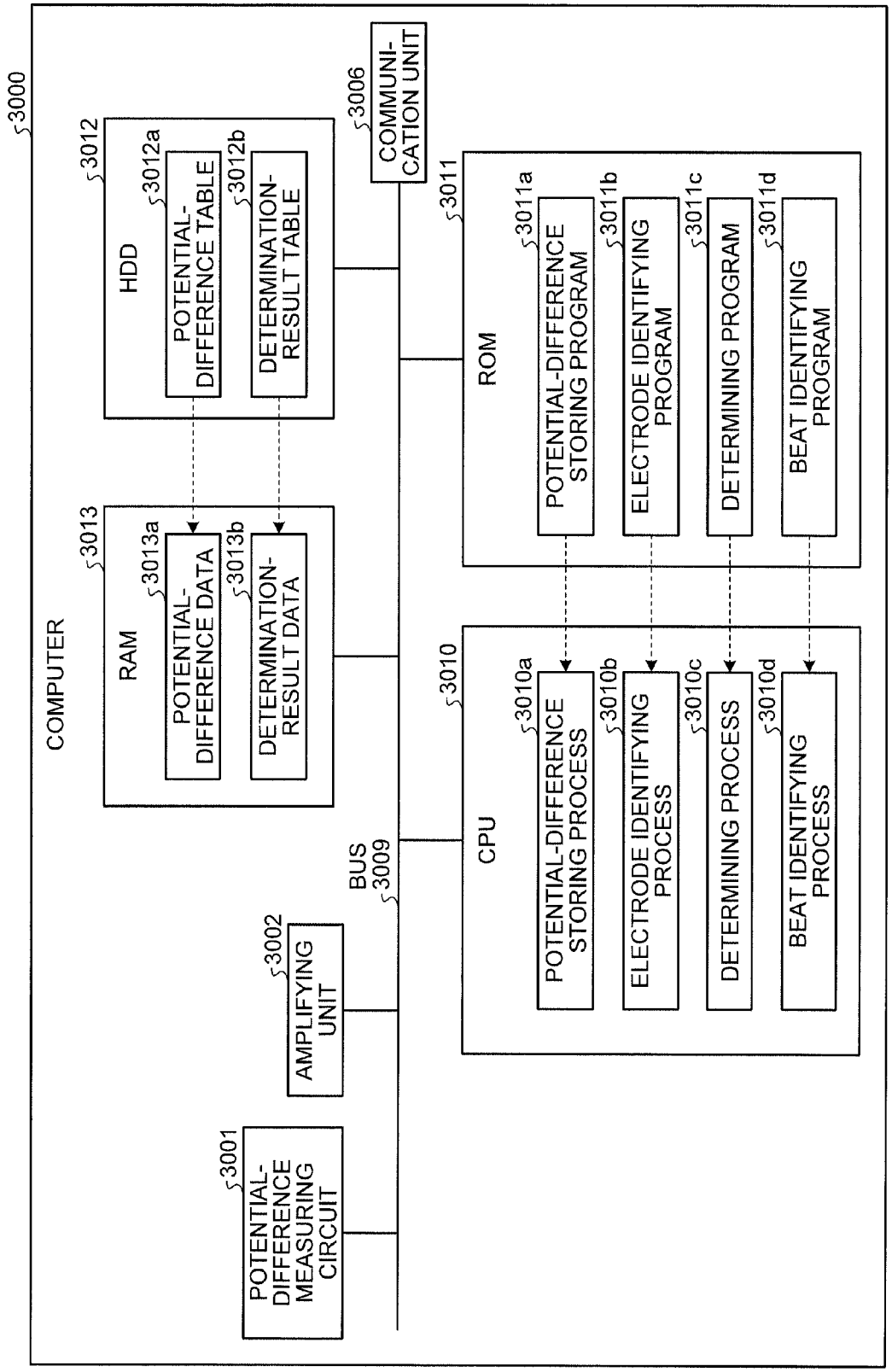
FIG. 15 is a diagram for explaining about an example of a computer that executes an identification program according to the second embodiment.

As illustrated in FIG. 15, a computer 3000 in the second embodiment is composed of a potential-difference measuring circuit 3001, an amplifying unit 3002, a communication unit 3006, a CPU 3010, a ROM 3011, an HDD 3012, and a RAM 3013 that are connected by a bus 3009 and the like. Incidentally, the potential-difference measuring circuit 3001 corresponds to the potential-difference measuring unit 204 in FIG. 2, and the amplifying unit 3002 corresponds to the amplifying unit 205 in FIG. 2.

In the ROM 3011, a control program that fulfills the same functions as the potential-difference storing unit 401, the electrode identifying unit 402, the determining unit 403, and the beat identifying unit 404 illustrated in the above second embodiment, i.e., a potential-difference storing program 3011a, an electrode identifying program 3011b, a determining program 3011c, and a beat identifying program 3011d are stored in advance as illustrated in FIG. 15. Incidentally, these programs 3011a to 3011d can be arbitrarily integrated or dispersed in the same manner as the elements of the identification device 200 illustrated in FIG. 2.

The CPU 3010 reads these programs 3011a to 3011d from the ROM 3011 and executes these programs 3011a to 3011d, thereby the programs 3011a to 3011d work as a potential-difference storing process 3010a, an electrode identifying process 3010b, a determining process 3010c, and a beat identifying process 3010d, respectively, as illustrated in FIG. 15. Incidentally, the processes 3010a to 3010d correspond to the potential-difference storing unit 401, the electrode identifying unit 402, the determining unit 403, and the beat identifying unit 404 illustrated in FIG. 2, respectively.

In the HDD 3012, a potential-difference table 3012a and a determination-result table 3012b are stored. Incidentally, the tables 3012a and 3012b correspond to the potential-difference storage unit 301 and the determination-result storage unit 302 illustrated in FIG. 2, respectively.

Then, the CPU 3010 reads the potential-difference table 3012a and the determination-result table 3012b and stores data on the tables 3012a and 3012b in the RAM 3013, and executes an identification program using the potential-difference data 3013a and determination-result data 3013b stored in the RAM 3013.

Others

Incidentally, the identification program described in the present embodiment can be distributed via a network, such as the Internet. Furthermore, the identification program can be recorded on a computer-readable recording medium, such as a hard disk, a flexible disk (FD), a CD-ROM, an MO, or a DVD, and the computer can execute the identification program by reading out the identification program from the recording medium.

According to an aspect of an identification device disclosed herein, the identification device can distinguish whether the right hand or the left hand is in contact with an electrode installed in a wheel.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An identification device comprising:
a measuring unit configured to measure a potential difference signal between two contact electrodes which are contacted by a driver, one electrode of the two electrodes is from among a plurality of electrodes installed in a handling unit of a vehicle, and the other electrode is from among the plurality of electrodes or an electrode which is different from the plurality of electrodes installed in the handling unit;
an electrode identifying unit configured to identify an electrode which is contacted by the driver from among the plurality of electrodes installed in the handling unit;
a determining unit configured to acquire a rotational state of the handling unit from a control device of the vehicle, and determine whether a driver's hand, which is in contact with the electrode identified, is the right hand or the left hand on the basis of the rotational state of the handling unit and a position of the electrode identified in the handling unit; and a beat identifying unit configured to identify a heart beat from the potential difference signal which is amplified by an amplification factor, the amplification factor being determined on the basis of a result of determination by the determining unit.

2. The identification device according to claim 1, further comprising a determination-result storage unit configured to store therein a result of determination by the determining unit and identification information identifying an electrode which is contacted by the driver in an associated manner, wherein the electrode identifying unit includes identifying whether the plurality of electrodes installed in the handling unit is contacted by driver's both hands or one hand, and when the electrode identifying unit identifies that an electrode is contacted by driver's one hand, the determining unit includes reading out a previous result from the determination-result storage unit, the result associated with identification information identifying the electrode identified by the electrode identifying unit, and when the read previous result indicates that the electrode is contacted by the right hand, the determining unit includes determining that the electrode is contacted by the right hand, when the read previous result indicates that the electrode is contacted by the left hand, the determining unit includes determining that the electrode is contacted by the left hand.

3. The identification device according to claim 1, wherein when a handling-unit potential difference signal, which is a potential difference signal between two electrodes which are contacted by the driver, each electrode is from among the plurality of electrodes installed in the handling unit, is measured by the measuring unit, the beat identifying unit includes identifying the heart rate signal using the handling unit potential difference signal, and when no handling unit potential difference signal is measured by the measuring unit, the beat identifying unit includes identifying the heart rate signal using a potential difference signal between electrode from among the plurality of electrodes installed in the handling unit and the other electrode which is different from the plurality of electrodes installed in the handling unit.

4. An identification apparatus comprising:
a processor; and
a memory, wherein the processor configured to executes:
measuring a potential difference signal between two electrodes which are contacted by a driver, one electrode of the two electrodes is from among a plurality of electrodes installed in a handling unit of a vehicle, and the other electrode is from among the plurality of electrodes or an electrode which is different from the plurality of electrodes installed in the handling unit;
identifying an electrode which is contacted by the driver from among the plurality of electrodes installed in the handling unit;
acquiring a rotational state of the handling unit from a control device of the vehicle, and determining whether a driver's hand, which is in contact with the electrode identified, is the right hand or the left hand on the basis of the rotational state of the handling unit and a position of the electrode identified in the handling unit; and
identifying a heart beat from the potential difference signal which is amplified by an amplification factor, the amplification factor being determined on the basis of a result of determination by the determining.

5. An identification method comprising:
measuring a potential difference signal between two electrodes which are contacted by a driver, one electrode of the two electrodes is from among a plurality of electrodes installed in a handling unit of a vehicle, and the other electrode is from among the plurality of electrodes or an electrode which is different from the plurality of electrodes installed in the handling unit;
identifying an electrode which is contacted by the driver from among the plurality of electrodes installed in the handling unit;
acquiring a rotational state of the handling unit from a control device of the vehicle, and determining whether a driver's hand, which is in with the contact electrode identified, is the right hand or the left hand on the basis of the rotational state of the handling unit and a position of the electrode identified in the handling unit; and
identifying a heart beat from the potential difference signal which is amplified by an amplification factor, the amplification factor being determined on the basis of a result of determination by the determining.

6. A non-transitory computer readable storage medium having stored therein an identification program causing a computer to execute a process comprising:
measuring a potential difference signal between two electrodes which are contacted by a driver, one electrode of the two electrodes is from among a plurality of electrodes installed in a handling unit of a vehicle, and the other electrode is from among the plurality of electrodes or an electrode which is different from the plurality of electrodes installed in the handling unit;
identifying an electrode which is contacted by the driver from among the plurality of electrodes installed in the handling unit;
acquiring a rotational state of the handling unit from a control device of the vehicle, and determining whether a driver's hand, which is in contact with the electrode identified, is the right hand or the left hand on the basis of the rotational state of the handling unit and a position of the electrode identified in the handling unit; and
identifying a heart beat from the potential difference signal which is amplified by an amplification factor, the amplification factor being determined on the basis of a result of determination by the determining.

* * * * *

UNITED STATES PATENT AND TRADEMARK OFFICE
CERTIFICATE OF CORRECTION

| | |
|---|---|
| PATENT NO. | : 8,731,645 B2 |
| APPLICATION NO. | : 13/353735 |
| DATED | : May 20, 2014 |
| INVENTOR(S) | : Hideo Kato |

It is certified that error appears in the above-identified patent and that said Letters Patent is hereby corrected as shown below:

In the Claims

Column 26, Line 25, Claim 5, delete "in with" and insert -- in contact with --, therefor.

Column 26, Line 25, Claim 5, "contact electrode" and insert -- electrode --, therefor.

Signed and Sealed this
Fourth Day of November, 2014

Michelle K. Lee
*Deputy Director of the United States Patent and Trademark Office*